(12) United States Patent
Skaar et al.

(10) Patent No.: US 8,916,163 B1
(45) Date of Patent: Dec. 23, 2014

(54) METHOD FOR TREATING MICROBIAL INFECTIONS

(75) Inventors: Eric Skaar, Brentwood, TN (US); Brian Corbin, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 756 days.

(21) Appl. No.: 12/341,848

(22) Filed: Dec. 22, 2008

Related U.S. Application Data

(60) Provisional application No. 61/015,825, filed on Dec. 21, 2007.

(51) Int. Cl.
*A61K 39/00* (2006.01)
*A61K 39/38* (2006.01)

(52) U.S. Cl.
USPC ..................................... 424/184.1; 424/185.1

(58) Field of Classification Search
None
See application file for complete search history.

(56) References Cited

U.S. PATENT DOCUMENTS

| | | | | |
|---|---|---|---|---|
| 5,731,008 A * | 3/1998 | Morrow | | 424/613 |
| 6,706,683 B1 * | 3/2004 | Seto et al. | | 514/13.5 |
| 2003/0170174 A1 * | 9/2003 | Liu | | 424/1.11 |
| 2006/0045855 A1 * | 3/2006 | Sasson | | 424/53 |

OTHER PUBLICATIONS

Sohnle et al (The Journal of Infectious Disease, 200;182:1272-5).*
Lusitani et al (Infection and Immunity, Aug. 2003, Vo. 71, No. 8, p. 4711-4716).*
Yui et al (Biol. Pham. Bull. 26(60:753-760, Jun. 2003).*
Herndon et al (J Lab Clin Med, vol. 141, No. 2, p. 110-120).*
Schroder et al (Drug Discovery Today: Therapeutic Strategies, vol. 3, No. 1, 2006, p. 93-100).*
Macmillan et al (Vanderbilt Medicine, vol. 23, No. 2, p. 35-38, Fall 2006).*
Sohnle et al (The Journal of Infectious Disease vol. 182, pp. 1272-1275, 2000).*
Herndon et al (J. Lab Clin Med, vol. 141, No. 2, pp. 110-120, 2003).*
Voyich et al, Insights into mechanisms used by *Staphylococcus aureus* to avoid destruction by human neutrophils, J Immunol 175, 3907 (Sep. 15, 2005).
Dale, et al., Distribution of a new myelomonocytic antigen (L1) in human peripheral blood leukocytes, Am J Clin Pathol 84, 24 (Jul. 1985).
Odink et al, Two calcium-binding proteins in infiltrate macrophages of rheumatoid arthritis, Nature 330, 80 (Nov. 5-11, 1987).
Wilkinson et al., Expression pattern of two related cystic fibrosis-associated calcium-binding proteins in normal and abnormal tissues, J Cell Sci 91 ( Pt 2), 221 (Oct. 1988).
Steinbakk et al., Antimicrobial actions of calcium binding leucocyte L1 protein, calprotectin, Lancet 336, 763 (Sep. 29, 1990).
Loomans, et al, Histidine-based zinc-binding sequences and the antimicrobial activity of calprotectin, J Infect Dis 177, 812 (Mar. 1998).
Lusitani, et al, Calprotectin, an abundant cytosolic protein from human polymorphonuclear leukocytes, inhibits the growth of *Borrelia burgdorferi*, Infect Immun 71, 4711 (Aug. 2003).
Sohnle, et al., Zinc-reversible antimicrobial activity of recombinant calprotectin (migration inhibitory factor-related proteins 8 and 14), J Infect Dis 182, 1272 (Oct. 2000).
Sugarman, B., Zinc and Infection, Rev Infect Dis 5, 137 (Jan.-Feb. 1983).
Murthy, et al., In vitro candidastatic properties of the human neutrophil calprotectin complex, JImmunol 151, 6291 (Dec. 1, 1993).
Hunter, et al., High level expression and dimer characterization of the S100 EF-hand proteins, migration inhibitory factor-related proteins 8 and 14, JBiol Chem 273, 12427 (May 15, 1998).
Clohessy, et al., Calprotectin-mediated zinc chelation as a biostatic mechanism in host defence, Immunol 42, 551 (Nov. 1995).
Johne et al., Functional and clinical aspects of the myelomonocyte protein calprotectin, Mol Pathol 50, 113 (Jun. 1997).
Voganatsi, Mechanism of extracellular release of human neutrophil calprotectin complex, JLeukoc Biol 70, 130 (Jul. 2001).
Korndorfer, et al., The crystal structure of the human (S100A8/S100A9)2 heterotetramer, calprotectin, illustrates how conformational changes of interacting a-helices can determine specific association of two EF-hand proteins, JMol Biol 370, 887 (Jul. 27, 2007).
Delabie, et al., Differential expression of the calcium-binding proteins MRP8 and MRP14 in granulomatous conditions: an immunohistochemical study, Clin Exp Immunol 81, 123 (Jul. 1990).
Robinson, et al., the S100 family heterodimer, MRP-8/14, binds with high affinity to heparin and heparan sulfate glycosaminoglycans on endothelial cells, JBiol Chem 277, 3658 (Feb. 1, 2002).
Horsburgh et al., MntR modulates expression of the PerR regulon and superoxide resistance in *Staphylococcus aureus* through control of manganese uptake, Mol Microbiol 44, 1269 (Jun. 2002).
Passey, et al., A null mutation in the inflammation-associated S100 protein 5100A8 causes early resorption of the mouse embryo, JImmunol 163, 2209 (Aug. 15, 1999).
Vogl et al., Mrp8 and Mrp9 are endogenous activators of toll-like receptor 4, promoting lethal, endotoxin-induced shock, Nat Med 13, 1042 (Sep. 2007).
Duthie, et al., Staphylococcal coagulase: mode of action and antigenicity, J Gen Microbiol 6, 95 (Feb. 1952).
Bae et al., *Staphylococcus aureus* virulence genes identifid by bursa aurealis mutagenesis and nematode killing, Proc Natl Acad Sci USA 101, 12312 (Aug. 17, 2004).
Yui, et al., Implication of extracellular zinc exclusion by recombinant human calprotectin (MRP8 and MRP14) from target cells in its apoptosis-inducing activity, Mediators Inflamm 11, 165 (Jun. 2002).
Verdrengh, et al., Role of neutrophils in experimental septicemia and septic arthritis induced by *Staphylococcus aureus*, Infect Immun 65, 2517 (Jul. 1997).
Vassiloyanakopoulos, et al., The crucial role of polymorphonuclear leukocytes in resistance to *Salmonella* dublin infections in genetically susceptible and resistant mice, Proc Natl Acad Sci USA 95, 7676 (Jun. 23, 1998).
Corbin, et al., Metal chelation and inhibition of bacterial growth in tissue abscesses., Science 319, pp. 962-965, Feb. 15, 2008.

* cited by examiner

*Primary Examiner* — Albert Navarro
(74) *Attorney, Agent, or Firm* — Stites & Harbison PLLC; Mandy Wilson Decker

(57) ABSTRACT

A method for treating a microbial infection or an abscessed tissue in a subject includes administering to the subject an effective amount of a metal ion chelator. In some embodiments, the metal ion chelator can be a protein, such as a calprotectin heterodimer. In some embodiments, the metal ion chelator is a calprotectin heterodimer including an S100A8 polypeptide and an S100A9 polypeptide.

26 Claims, 8 Drawing Sheets

SEQUENCE LISTING

```
<160> NUMBER OF SEQ ID NOS: 8

<210> SEQ ID NO 1
<211> LENGTH: 94
<212> TYPE: PRT
<213> ORGANISM: Homo sapiens
```

-continued

<400> SEQUENCE: 1

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His His Lys Glu
                85                  90

<210> SEQ ID NO 2
<211> LENGTH: 114
<212> TYPE: PRT
<213> ORGANISM: Homo sapiens

<400> SEQUENCE: 2

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His Lys Pro Gly Leu Gly Glu Gly
            100                 105                 110

Thr Pro

<210> SEQ ID NO 3
<211> LENGTH: 89
<212> TYPE: PRT
<213> ORGANISM: Mus musculus

<400> SEQUENCE: 3

Met Pro Ser Glu Leu Glu Lys Ala Leu Ser Asn Leu Ile Asp Val Tyr
1               5                   10                  15

His Asn Tyr Ser Asn Ile Gln Gly Asn His His Ala Leu Tyr Lys Asn
            20                  25                  30

Asp Phe Lys Lys Met Val Thr Thr Glu Cys Pro Gln Phe Val Gln Asn
        35                  40                  45

Ile Asn Ile Glu Asn Leu Phe Arg Glu Leu Asp Ile Asn Ser Asp Asn
    50                  55                  60

Ala Ile Asn Phe Glu Glu Phe Leu Ala Met Val Ile Lys Val Gly Val
65                  70                  75                  80

Ala Ser His Lys Asp Ser His Lys Glu
                85

```
<210> SEQ ID NO 4
<211> LENGTH: 113
<212> TYPE: PRT
<213> ORGANISM: Mus musculus

<400> SEQUENCE: 4

Met Ala Asn Lys Ala Pro Ser Gln Met Glu Arg Ser Ile Thr Thr Ile
1               5                   10                  15

Ile Asp Thr Phe His Gln Tyr Ser Arg Lys Glu Gly His Pro Asp Thr
            20                  25                  30

Leu Ser Lys Lys Glu Phe Arg Gln Met Val Glu Ala Gln Leu Ala Thr
        35                  40                  45

Phe Met Lys Lys Glu Lys Arg Asn Glu Ala Leu Ile Asn Asp Ile Met
    50                  55                  60

Glu Asp Leu Asp Thr Asn Gln Asp Asn Gln Leu Ser Phe Glu Glu Cys
65                  70                  75                  80

Met Met Leu Met Ala Lys Leu Ile Phe Ala Cys His Glu Lys Leu His
                85                  90                  95

Glu Asn Asn Pro Arg Gly His Gly His Ser His Gly Lys Gly Cys Gly
            100                 105                 110

Lys

<210> SEQ ID NO 5
<211> LENGTH: 49
<212> TYPE: DNA
<213> ORGANISM: Artificial Sequence
<220> FEATURE:
<223> OTHER INFORMATION: Primer

<400> SEQUENCE: 5
ggggacaagt ttgtacaaaa aagcaggcta ctgtaccaca aactatccc            49

<210> SEQ ID NO 6
<211> LENGTH: 31
<212> TYPE: DNA
<213> ORGANISM: Artificial Sequence
<220> FEATURE:
<223> OTHER INFORMATION: Primer

<400> SEQUENCE: 6
ccccgtcgac ccattattcg taaggattgc c                               31

<210> SEQ ID NO 7
<211> LENGTH: 50
<212> TYPE: DNA
<213> ORGANISM: Artificial Sequence
<220> FEATURE:
<223> OTHER INFORMATION: Primer

<400> SEQUENCE: 7
ggggaccact ttgtacaaga aagctgggta ggtaagtcta agtctaacg             50

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ccccgtcgac gtcagttacg aaaatgcaat g                               31
```

METHOD FOR TREATING MICROBIAL INFECTIONS

RELATED APPLICATIONS

This application claims priority from U.S. Provisional Application Ser. No. 61/015,825 filed Dec. 21, 2007, the entire disclosure of which is incorporated herein by this reference.

GOVERNMENT INTEREST

Subject matter described herein was made with U.S. Government support under Grant Number T32 HL069765 awarded by the National Institute of Health. Studies described herein were also supported by awards to Dr. Eric P. Skaar from the Searle Scholars Fund and the Burroughs Wellcome Fund. The government has certain rights in the described subject matter.

TECHNICAL FIELD

The presently-disclosed subject matter relates to treatment of microbial infections. In particular, the presently-disclosed subject matter relates to treatment of abscessed tissue caused by microbial infections.

BACKGROUND

Undesirable infections can be caused by a variety of microbes, including microbes such as fungi and antibacterial-resistant bacteria that are notoriously difficult to treat. Such microbial infections are sometimes capable of causing an abscess in a subject. An abscess is a localized accumulation of pus and/or inflammation in a tissue or organ. An abscess can form, for example, on the skin or on other tissues or organs of the subject, causing swelling and pain.

Traditional treatment for abscesses includes piercing or cutting open the abscess to remove the puss and infectious material, and treatment with antibiotics, e.g., oral, topical, injectable. Depending on the size and the location of the abscess, such traditional treatment can be successful; however, for certain abscesses, e.g., relatively large abscesses, and/or abscesses caused by antibiotic-resistant bacteria or otherwise resistant microbes, such traditional treatment can be insufficiently effective.

Accordingly, there remains a need in the art for effective methods for treating microbial infections and abscessed tissues.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes a method for treating a microbial infection or an abscessed tissue in a subject. The method includes administering to the subject an effective amount of a metal ion chelator.

In some embodiments, the metal ion chelator is a $Mn^{2+}$ chelator. In some embodiments, the metal ion chelator is a $Mn^{2+}$ and $Zn^{2+}$ chelator.

In some embodiments, the metal ion chelator is a protein metal ion chelator. In some embodiments, the protein metal ion chelator is a calprotectin heterodimer, or a functional fragment or a functional variant of a calprotectin heterodimer. In some embodiments, the calprotectin heterodimer is bound with $Ca^{2+}$ before administration.

In some embodiments, the calprotectin heterodimer can include an S100A8, or functional fragment or functional variant thereof, and an S100A9 polypeptide, or functional fragment or functional variant thereof. In some embodiments, the S100A8 polypeptide can include the amino acid sequence of SEQ ID NO: 1. In some embodiments, the S100A8 polypeptide can include the amino acid sequence of SEQ ID NO: 3. In some embodiments, the S100A9 polypeptide can include the amino acid sequence of SEQ ID NO: 2. In some embodiments, the S100A9 polypeptide can include the amino acid sequence of SEQ ID NO: 4.

In some embodiments, the calprotectin heterodimer can include the S100A8 polypeptide including the amino acid sequence of SEQ ID NO: 1, and the S100A9 polypeptide including the amino acid sequence of SEQ ID NO: 2. In some embodiments, the calprotectin heterodimer can include the S100A8 polypeptide including the amino acid sequence of SEQ ID NO: 3, and the S100A9 polypeptide including the amino acid sequence of SEQ ID NO: 4.

In some embodiments in which the calprotectin heterodimer includes a functional fragment or functional variant of the S100A8 polypeptide and/or the S100A9 polypeptide, both the S100A8 polypeptide and the S100A9 polypeptide include a preserved metal ion binding motif.

In some embodiments, the method is for treating a microbial infection or an abscessed tissue caused by a bacterial pathogen. In some embodiments, the bacterial pathogen is an antibiotic-resistant strain of a bacterial pathogen. In some embodiments, the bacterial pathogen is selected from: *Bacillus anthracis, Enterococcus faecalis, Staphylococcus aureus, Streptococcus pneumonia, Pseudomonas aeruginosa, Escherichia coli, Salmonella typhimurium,* and *Acinetobacter baumannii.* In some particular embodiments, the bacterial pathogen is a *Staphylococcus.* In some particular embodiments, the bacterial pathogen is *Staphylococcus aureus.*

In some embodiments, the method is for treating a microbial infection or an abscessed tissue caused by a fungal pathogen. In some embodiments, the fungal pathogen is selected from: *Candida albicans, Toxoplasma gondii,* and *Cryptococcus neoformans.*

In some embodiments of the method for treating a microbial infection or an abscessed tissue, the metal ion chelator is administered before the microbial infection or the abscessed tissue occurs in the subject. In some embodiments, the metal ion chelator is administered after the microbial infection or the abscessed tissue occurs in the subject.

In some embodiments, the metal ion chelator is administered to the abscessed tissue. In some embodiments, the metal ion chelator is administered at or near a site of infection. In some embodiments, the metal ion chelator is administered at or near a site associated with a risk of infection. In some embodiments, the metal ion chelator is administered topically. In some embodiments, the metal ion chelator is administered by injection.

The presently-disclosed subject matter includes a kit for use in treating a microbial infection or an abscessed tissue. In some embodiments, the kit includes a vial containing a metal ion chelator, and instructions for treating a microbial infection or an abscessed tissue in a subject. In some embodiments, the metal ion chelator is a calprotectin heterodimer. In some embodiments, the calprotectin heterodimer is $Ca^{2+}$-bound. In some embodiments, the kit further includes a vial containing a $Ca^{2+}$-containing buffer.

BRIEF DESCRIPTION OF THE DRAWINGS

FIGS. 2C-2F include photographs of representative sections of tissue from uninfected or infected mice immunostained for S100A8.

BRIEF DESCRIPTION OF THE SEQUENCE LISTING

Figure 1:
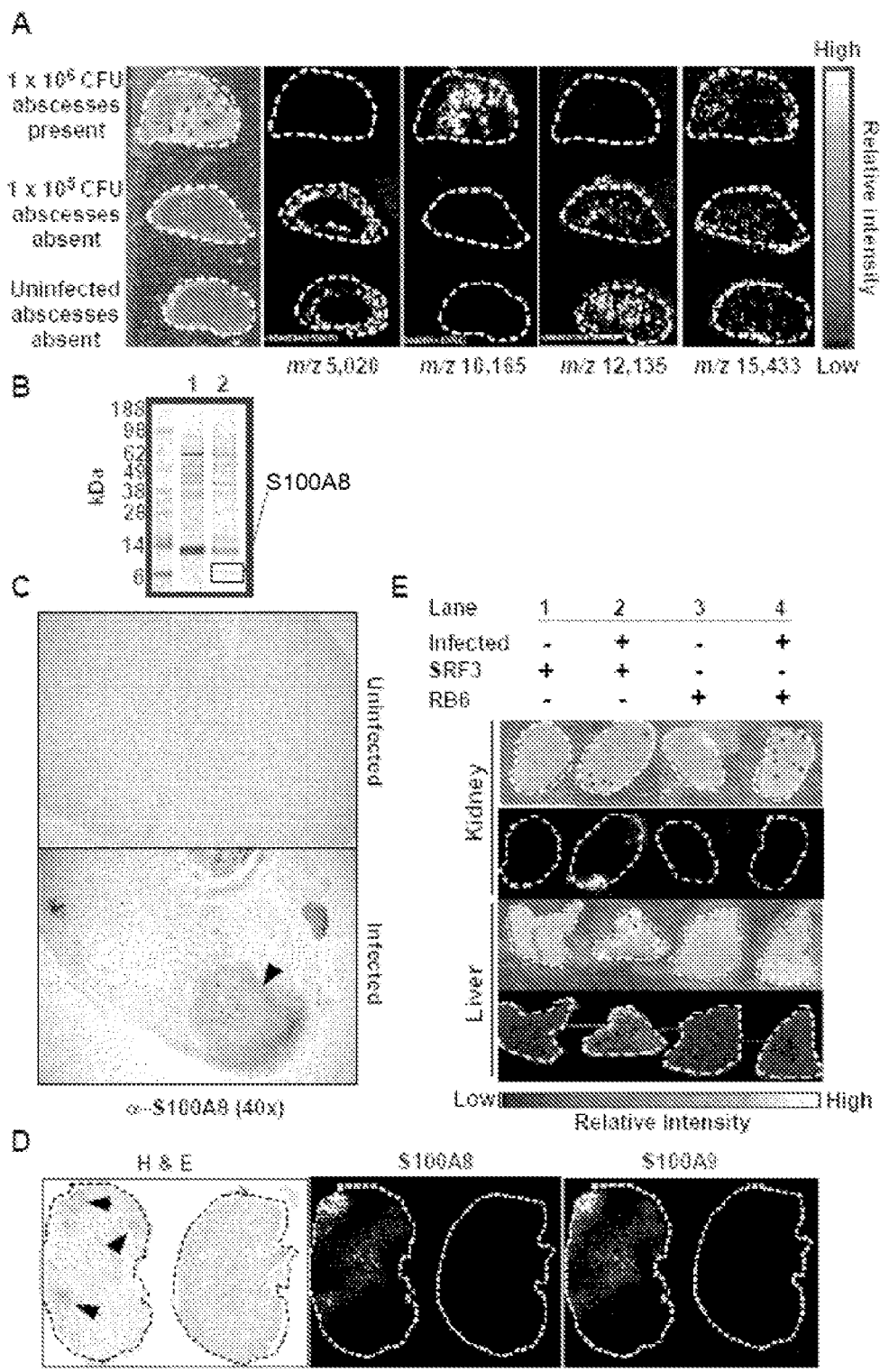
FIG. 1A includes mass spectrometric images of S. aureus infected and uninfected murine kidneys.
FIG. 1B includes results of SDS-PAGE analysis of material extracted from kidneys of uninfected (lane 1) or infected (lane 2) mice followed by MS/MS-based identification of proteins.
FIG. 1C includes results from immunohistochemistry studies showing α-S100A8 antisera localizes S100A8 to S. aureus-infected murine abscesses.
FIG. 1D includes mass spectrometric images of S. aureus infected and uninfected murine kidneys, showing the distribution of S100A8 (m/z 10,165) and S100A9 (m/z 12,976).
FIG. 1E includes images from a mass spectrometry analyses of S100A8 expression within kidneys and livers from neutrophil replete uninfected mice (lane 1), neutrophil replete infected mice (lane 2), neutrophil-depleted uninfected mice (lane 3), and neutrophil-depleted infected mice (lane 4), where the top row in each organ set shows matrix treated organs, and the bottom row in each organ set shows IMS.
Figure 2:
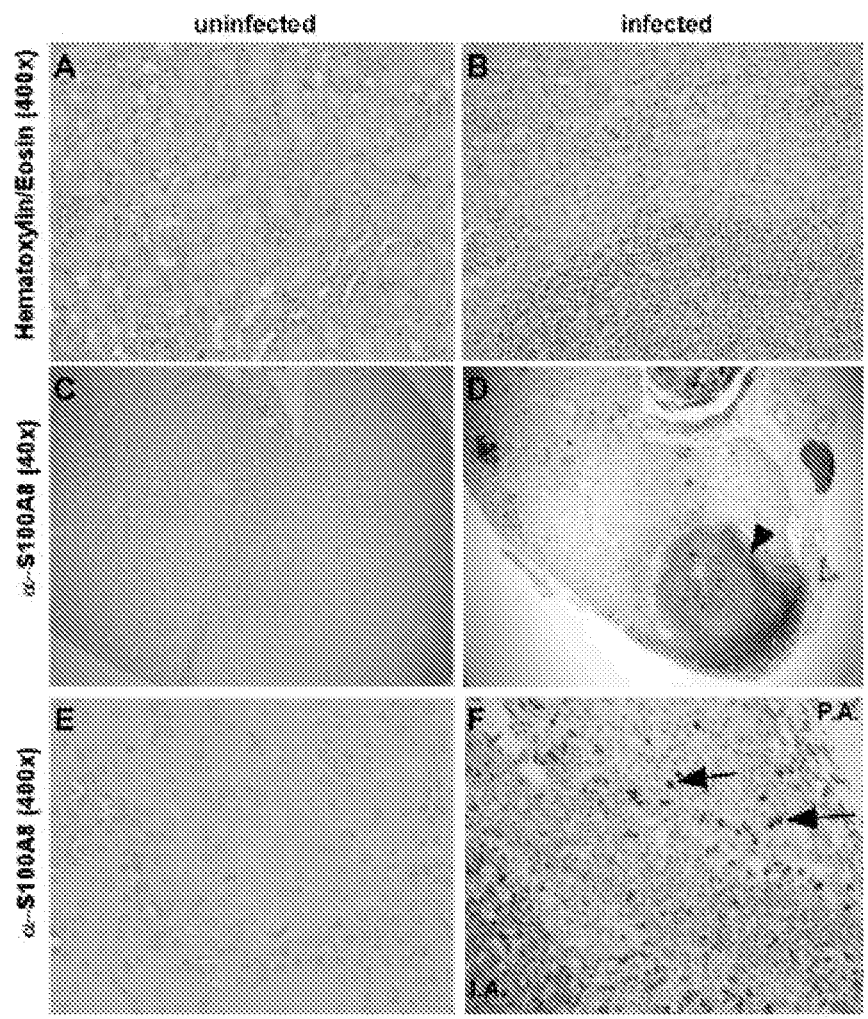
FIGS. 2A-2F include the results of a histological analysis of kidney tissue sections harvested from uninfected or infected mice 96 hr post-infection. Kidney sections from (FIG. 2A) uninfected and (FIG. 2B) infected C57BL/6 mice were stained with hematoxylin and eosin to assess inflammation.

SEQ ID NO: 1 is a human S100A8 polypeptide.
SEQ ID NO: 2 is a human S100A9 polypeptide.
SEQ ID NO: 3 is a Mus musculous S100A8 polypeptide.
SEQ ID NO: 4 is a Mus musculous S100A9 polypeptide.

SEQ ID NO: 5 is a primer, SAV0634-5'1-AttB1.
SEQ ID NO: 6 is a primer, SAV0634-3'1-SalI.
SEQ ID NO: 7 is a primer, SAV0634-3'2-AttB2.
SEQ ID NO: 8 is a primer, SAV0634-5'2-SalI.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes methods for treating a microbial infection and/or treating an abscessed tissue in a subject, including administering to the subject an effective amount of a metal ion chelator.

As used herein, the term "microbial infection" refers to an infection by a microbe. The term "microbe" refers to a non-viral pathogen, including all bacterial pathogens and all fungal pathogens. The term microbial infection further refers to antibiotic-resistant strains of bacterial pathogens.

As used herein, the term "bacterial pathogen" refers to a bacteria capable of causing infection in a subject. In some embodiments, a bacterial pathogen is capable of causing an abscessed tissue. Examples of bacterial pathogens include, but are not limited to, gram positive bacterial pathogens including, *Bacillus anthracis, Enterococcus faecalis, Staphylococcus aureus*, and *Streptococcus pneumonia*; gram negative bacterial pathogens including, *Pseudomonas aeruginosa, Escherichia coli, Salmonella typhimurium*, and *Acinetobacter baumannii*.

As used herein when referring to a bacterial pathogen, the term "antibiotic-resistant strain" refers to a bacterial pathogen that is capable of withstanding an effect of an antibiotic used in the art to treat the bacterial pathogen (i.e., a non-resistant strain of the bacterial pathogen). For example, *Staphylococcus aureus* can be treated using methicillin; however, an antibiotic-resistant strain of *Staphylococcus aureus* is methicillin-resistant *Staphylococcus aureus* (MRSA).

As used herein, the term "fungal pathogen" refers to a fungus capable of causing infection in a subject. In some embodiments, a fungal pathogen is capable of causing an abscessed tissue. Examples of fungal pathogens include, but are not limited to, *Candida albicans, Toxoplasma gondii*, and *Cryptococcus neoformans*.

The terms "abscessed tissue" and "abscess" refers to a localized accumulation of pus and/or inflammation in a tissue or organ, e.g., skin, that is caused by a microbial infection.

As used herein, the terms "treatment" or "treating" relate to any treatment of a microbial infection, or an abscessed tissue caused by a microbial infection, including therapeutic, (i.e., post-infection), and prophylactic treatment, (i.e., pre-infection). Although most commonly therapeutic treatment will be affected, prophylactic treatment can be useful in cases that will be recognized by one of ordinary skill in the art, for example, prophylactic treatment to prevent surgical site infection. As such, the terms treatment or treating include, but are not limited to: preventing a microbial infection or an abscess or the development of a microbial infection or an abscess; inhibiting the progression of a microbial infection or an abscess; arresting or preventing the development of a microbial infection or an abscess; reducing the severity of a microbial infection or an abscess; ameliorating or relieving symptoms associated with a microbial infection or an abscess; and causing a regression of a microbial infection or an abscess or one or more of the symptoms associated with a microbial infection or an abscess. In some cases, in addition to making use of the methods described herein, it can be desirable to make use of traditional and other known treatment protocols such as surgical drainage of an abscess. Although such traditional and other known treatment protocols will not be described in any detail herein, they will be known and understood by those skilled in the art, and it is contemplated that such traditional and other known treatment protocols can be used in combination with the methods and compositions described herein, if desired.

As used herein, the term "subject" refers to humans, and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

In accordance with the methods of the presently-disclosed subject matter, a metal ion chelator can be administered to treat the microbal infection and/or abscessed tissue of the subject.

As used herein the term "metal ion chelator" refers to an agent capable of sequestering metal ions. In some embodiments, the metal ion chelator can be a manganese ion ($Mn^{2+}$) chelator, capable of sequestering $Mn^{2+}$. In some embodiment the metal ion chelator is a manganese ion ($Mn^{2+}$) chelator and a zinc ion ($Zn^{2+}$) chelator, capable of sequestering both $Mn^{2+}$ and $Zn^{2+}$. Without wishing to be bound by theory or mechanism, it is believed that the metal ion chelators of the presently-disclosed subject matter bind $Mn^{2+}$, depriving the microbe of this growth factor; in the absence of available $Mn^{2+}$ the microbe becomes unable to survive.

In some embodiments, the metal ion chelator is a polypeptide capable of sequestering $Mn^{2+}$ (or $Mn^{2+}$ and $Zn^{2+}$), i.e., a polypeptide or protein metal ion chelator. In some embodiments, the polypeptide is an isolated polypeptide capable of sequestering $Mn^{2+}$ (or $Mn^{2+}$ and $Zn^{2+}$).

The terms "polypeptide," "protein," and "peptide," which are used interchangeably herein, refer to a polymer of the 20 protein amino acids, or amino acid analogs, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted.

The term "isolated", when used in the context of an isolated protein is a protein that, by the hand of man, exists apart from its native environment and is therefore not a product of nature. An isolated protein or polypeptide can exist in a purified form or can exist in a non-native environment such as, for example, in a transgenic host cell. In some embodiments, the term "isolated", when applied to a protein, denotes that the protein is essentially free of other cellular components with which it is associated in nature. It can be in a homogeneous state although it can be in either a dry or aqueous solution. Homogeneity and whether a molecule is isolated can be determined using analytical chemistry techniques such as polyacrylamide gel electrophoresis or high performance liquid chromatography. A polypeptide that is the predominant species present in a preparation is substantially isolated. The term "isolated" denotes that a polypeptide gives rise to essentially one band in an electrophoretic gel. Particularly, it means that the polypeptide is in some embodiments at least about 50% pure, 60% pure, 70% pure, 80% pure, 85% pure, 90% pure, 95% pure, or 99% pure.

In some embodiments, the polypeptide metal ion chelator can be calprotectin, which is capable of sequestering $Mn^{2+}$ (See Examples below). Calprotectin used in accordance with the presently-disclosed subject matter is a protein heterodimer, including an S100A8 polypeptide, and an S100A9 polypeptide. S100A8 polypeptides include, for example, *M. musculus* S100A8 (Accession Nos: NM_013650, NP_038678), *H. sapiens* S100A8 (Accession Nos: NM_002964, NP_002955), *R. norvegicus* S100A8 (Accession Nos: NM_053822, NP_446274). S100A9 polypeptides include, for example, *M. musculus* S100A9 (Accession Nos: NM_009114, NP_033140), *H. sapiens* S100A9 (Accession Nos: NM_002965, NP_002956), *R. norvegicus* S100A9 (Accession Nos: NM_053587, NP_446039).

In some embodiments, before calprotectin is administered it is bound with calcium ($Ca^{2+}$). Without wishing to be bound by theory or mechanism, it is believed that the ability of the calprotectin to sequester $Mn^{2+}$ (and $Zn^{2+}$) is enhanced or derived from the calprotectin being administered while bound to $Ca^{2+}$. It is further believed that process by which calprotectin binds $Mn^{2+}$ (and $Zn^{2+}$) includes the release of $Ca^{2+}$. In this regard, in some embodiments, calprotectin bound to $Ca^{2+}$ can be lyophilized, and resuspended in an appropriate buffer prior to administration. In some embodiments, calprotectin can be lyophilized, and resuspended in an appropriate buffer containing $Ca^{2+}$, wherein the calprotectin is allowed to bind to the $Ca^{2+}$ prior to administration. Appropriate buffers include, but are not limited to, phosphate-buffered saline (PBS) and any other physiologically-inert buffer, as can be identified by those of ordinary skill in the art.

In some embodiments, when a polypeptide metal ion chelator is used, it can be desirable to select a polypeptide, or appropriate fragment or variant thereof, having the same sequence as a polypeptide derived from the species of which the subject is a member, as will be understood by one of ordinary skill in the art. For example, when the subject is a human and the polypeptide metal ion chelator is calprotectin, it can be desirable to select human calprotectin, i.e., calprotectin heterodimer including human S100A8 (SEQ ID NO: 1), or a functional fragment or functional variant thereof, and human S100A9 (SEQ ID NO: 2), or a functional fragment or functional variant thereof.

In some embodiments, the metal ion chelator of the presently disclosed subject matter can be a functional fragment or a functional variant of calprotectin. As noted above, the calprotectin is a protein heterodimer, including an S100A8 polypeptide, and an S100A9 polypeptide. In this regard, a fragment and/or variant of calprotectin is a calprotectin heterodimer including a fragment or variant of S100A8 and/or a fragment or variant of S100A9. For example, a calprotectin fragment can include a fragment of S100A8 and a full-length S100A9. For another example, a calprotectin fragment can include a full-length S100A8 and a fragment of S100A9. For another example, a calprotectin fragment can include a fragment of S100A8 and a fragment of S100A9. For another example, a calprotectin variant can include a wild-type S100A8 and a S100A9 variant. For another example, a calprotectin variant can include a S100A8 variant and a wild-type S100A9. For another example, a calprotectin variant could include a S100A8 variant and a S100A9 variant.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both. Fragments typically are at least 10, 20, 30, 40, 50, 60, 70, 80, 90, or 100 amino acids long, depending on the reference polypeptide. A calprotectin fragment can be a calprotectin heterodimer including a S100A8 fragment, an S100A9 fragment, or both.

A fragment can also be a "functional fragment," in which the fragment retains some or all of the activity of the reference polypeptide as described herein. For example, in some embodiments, a functional fragment of a polypeptide metal ion chelator can retain some or all of the $Mn^{2+}$-sequestering activity of the reference polypeptide. In some embodiments, a functional fragment of a polypeptide metal ion chelator can retain some or all of the $Mn^{2+}$- and $Zn^{2+}$-sequestering activity of the reference polypeptide. In some embodiments, the functional fragment includes a preserved metal binding motif. In some embodiments, the functional fragment can include a $Mn^{2+}$ binding motif, a $Zn^{2+}$ binding motif, or both. In some embodiments, a fragment can comprise a domain or motif, and optionally additional amino acids on one or both sides of the domain or motif, which additional amino acids can number from 5, 10, 15, 20, 30, 40, 50, or more residues. A calprotectin functional fragment can be a calprotectin heterodimer including an S100A8 functional fragment, an S100A9 functional fragment, or both, so long as the resulting calprotectin functional fragment retains some or all of the activity of calprotectin.

The terms "variant" refer to an amino acid sequence that is different from the reference polypeptide by one or more amino acids, e.g., one or more amino acid substitutions. A variant of a reference polypeptide also refers to a variant of a fragment of the reference polypeptide, for example, a fragment wherein one or more amino acid substitutions have been made relative to the reference polypeptide. A variant can also be a "functional variant," in which the variant retains some or all of the activity of the reference protein as described herein. For example, a functional variant of a polypeptide metal ion chelator retains some or all of the $Mn^{2+}$-sequestering activity of the reference polypeptide. In some embodiments, a functional variant of a polypeptide metal ion chelator can retain some or all of the $Mn^{2+}$- and $Zn^{2+}$-sequestering activity of the reference polypeptide. In some embodiments, the functional variant includes a preserved metal binding motif. In some embodiments, the functional variant can include a $Mn^{2+}$, a $Zn^{2+}$ binding motif, or both, which binding motifs are preserved relative to the reference polypeptide. A calprotectin functional variant can be a calprotectin heterodimer including a S100A8 functional variant, an S100A9 functional variant, or both, so long as the resulting calprotectin functional variant retains some or all of the activity of calprotectin. The term functional variant does not include variants that loose the ability to inhibit microbial growth; for example, a human calprotectin variant wherein the cysteine residue at position 3 in S100A9 (SEQ ID NOS: 2) is replaced by another amino acid residue is not considered to be a functional variant (See Examples below).

The term functional variant includes a functional variant of a functional fragment of a reference polypeptide. The term functional variant further includes conservatively substituted variants. The term "conservatively substituted variant" refers to a peptide comprising an amino acid residue sequence that differs from a reference peptide by one or more conservative amino acid substitution, and maintains some or all of the activity of the reference peptide as described herein. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between threonine and serine; the substitution of one basic residue such as lysine or arginine for another; the substitution of one acidic residue, such as aspartic acid or glutamic acid for another; or the substitution of one aromatic residue, such as phenylalanine, tyrosine, or tryptophan for another. The phrase "conservatively substituted variant" also includes peptides wherein a residue is replaced with a chemically derivatized residue, provided that the resulting peptide maintains some or all of the activity of the reference peptide as described herein.

Without wishing to be bound by theory or mechanism, it is believed that the S100A8 and S100A9 polypeptides of SEQ ID NOS: 1-4 have metal binding motifs including particular amino acids identified in capitals in the sequences as set forth in Table A. In some embodiments, a calprotectin functional fragment includes a fragment of S100A8, a fragment of S100A9, or both, wherein each fragment includes a preserved metal ion binding motif. In some embodiments, a calprotectin variant includes a variant of S100A8, a variant of S100A9, or both, wherein each variant has a preserved metal ion binding motif.

TABLE A

Metal Ion Binding Motif

| Polypeptide | Sequence | SEQ ID NO |
|---|---|---|
| S100A8 (human) | mltelekaln siidvyhkys likgnfhavy rddlkkllet ecpqyirkkg advwfkeldi ntdgavnfqe flilvikmgv aahkks<u>HEESH</u>hke | 1 |
| S100A9 (human) | mtckmsqler nietiintfh qysvklghpd tlnqgefkel vrkdlqnflk kenknekvie himedldtna dkqlsfeefi mlmarltwas <u>HEKMH</u>egdeg pghhhkpglg egtp | 2 |
| S100A8 (murine) | mpselekals nlidvyhnys niqgnhhaly kndfkkmvtt ecpqfvqnin ienlfreldi nsdnainfee flamvikvgv as<u>HKDSH</u>ke | 3 |
| S100A9 (murine) | mankapsqme rsittiidtf hqysrkeghp dtlskkefrq mveaqlatfm kkekrneali ndimedldtn qdnqlsfeec mmlmaklifa c<u>HEKLH</u>ennp rghghshgkg cgk | 4 |

Calprotectin can be made for use in the presently-disclosed methods, for example, using molecular biology techniques known to those of ordinary skill in the art. Calprotectin heterodimers self assemble from S100A8 and S100A9 polypeptides. S100A8 and S100A9 polypeptides can be made, for example, using various molecular biology techniques known to those of ordinary skill in the art. Calprotectin, or a functional fragment or functional variant thereof, can be made by expressing S100A8 and S100A9, or functional fragments or functional variants thereof, within the same cell using molecular biology techniques known to those of ordinary skill in the art. The subunits heterodimerize within the cell, and calprotectin can be purified therefrom using molecular biology techniques known to those of ordinary skill in the art. Although $Ca^{2+}$ is not required to successfully express and purify calprotectin, as noted above, it can be useful in some embodiments to provide calprotectin that is bound with calcium ($Ca^{2+}$).

As noted above, the presently-disclosed subject matter includes methods for treating a microbial infection or an abscessed tissue in a subject, including administering an effective amount of a metal ion chelator to the subject.

The metal ion chelator can be locally administered at or near the site of infection (or site associated with a risk of infection), or the site of the abscessed tissue. For example, when the microbial infection is associated with the skin of the subject, the metal ion chelator can be administered topically. In some cases, the metal ion chelator can be injected into an abscess. Various methods of administrating the metal ion chelator can be used, as will be understood by one of ordinary skill in the art.

As used herein, an "effective amount" of the metal ion chelator is an amount sufficient to bind a desired amount of $Mn^{2+}$ (or $Mn^{2+}$ and $Zn^{2+}$) accessible to the microbe that is capable of causing an infection, causing an infection, or causing an abscess. In some embodiments, the effective amount of the metal ion chelator is an amount sufficient to bind substantially all of the $Mn^{2+}$ (or $Mn^{2+}$ and $Zn^{2+}$) accessible to the microbe. In some embodiments, the effective amount of the metal ion chelator is an amount sufficient to bind enough of the $Mn^{2+}$ (or $Mn^{2+}$ and $Zn^{2+}$) accessible to the microbe such that a treatment is affected. In some embodiments, an effective amount of the metal ion chelator is less than about 1 mg. In some embodiments when the metal ion chelator is administered by injection into an abscess, an effective amount of the metal ion chelator can be about 100 µg, about 90 µg, about 80 µg, about 70 µg, about 60 µg, or about 50 µg. In some embodiments, the metal ion chelator can be provided in a solution of about 70 µg/ml, and an appropriate volume can be administered such that an effective amount is provided.

Injectable formulations of the metal ion chelator can include various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). Physiologically-acceptable excipients can include, for example, 5% dextrose, 0.9% saline, Ringer's solution or other suitable excipients. A suitable insoluble form of the compound can be prepared and administered as a suspension in an aqueous base or a pharmaceutically-acceptable oil base, such as an ester of a long chain fatty acid, (e.g., ethyl oleate).

The metal ion chelator can also be provided in a cream or ointment, or in a transdermal patch for topical administration. A topical ointment formulation can contain the metal ion chelator in a carrier such as a pharmaceutical cream base. Various formulations for topical use include drops, tinctures, lotions, creams, solutions, and ointments containing the active ingredient and various supports and vehicles. The optimal percentage of the metal ion chelator in each formulation varies according to the formulation itself and the therapeutic effect desired in the specific situation.

The presently-disclosed subject matter further includes a kit for use in treating a microbial infection or an abscessed tissue in a subject. In some embodiments, the kit includes a metal ion chelator, and instructions for administering the metal ion chelator to the subject.

In some embodiments, the kit includes a metal ion chelator prepared for administration by injection. In this regard, the metal ion chelator can be provided in a vial, ready to be combined with an appropriate carrier for use in administering the metal ion chelator to the subject. In some embodiments, the metal ion chelator is provided in a single-dose vial, containing an amount of the metal ion chelator that is an effective amount for use in certain instances, e.g., effective amount for treatment in common instances. In some embodiments, the metal ion chelator is provided as a lyophilate. In some embodiments, the kit additionally includes a buffer for resuspending the lyophilate for administration to the subject. In some embodiments, the kit additionally includes instructions for preparing the metal ion chelator for administration.

In some embodiments, the kit includes a metal ion chelator prepared for topical administration. In this regard, the metal ion chelator can be provided in a cream or ointment, or in a transdermal patch.

In some embodiments, the kit includes a calprotectin heterodimer, or functional fragment or functional variant thereof.

In some embodiments, the kit includes a calprotectin heterodimer, or functional fragment or functional variant thereof, prepared for administration by injection. In this regard, the calprotectin heterodimer can be provided in a vial, ready to be combined with an appropriate carrier for use in administering the metal ion chelator to the subject. In some embodiments, the calprotectin heterodimer is provided as a lyophilate. In some embodiments, the lyophilate can be a $Ca^{2+}$-bound calprotectin heterodimer. In some embodiments, the kit can additionally include a buffer for resuspending the lyophilate for administration to the subject. In some embodiments, the lyophilate can be a calprotectin heterodimer that is free of $Ca^{2+}$. When the calprotectin heterodimer is free of $Ca^{2+}$, it can be resuspended in a buffer containing $Ca^{2+}$ prior to administration to the subject. In some embodiments, the kit additionally includes buffer containing $Ca^{2+}$ for resuspending the lyophilate for administration to the subject. In some embodiments, the kit additionally includes instructions for preparing the calprotectin heterodimer for administration.

In some embodiments, the kit includes a calprotectin heterodimer prepared for topical administration. In this regard, the calprotectin heterodimer can be provided as a $Ca^{2+}$-bound calprotectin heterodimer. The calprotectin heterodimer can be provided in a cream or ointment, or in a transdermal patch for topical administration.

The presently-disclosed subject matter is further illustrated by the following specific but non-limiting examples.

EXAMPLES

Abscesses represent an immune response to infection that confines the spread of disease through the restriction of microbial growth and dissemination to neighboring tissues. *Staphylococcus aureus* infection results in the formation of abscesses characterized by the extensive accumulation of host neutrophils (1). Although a role for neutrophils in abscess development is established, the specific host factors that limit microbial growth in the abscess are incompletely defined (1).

As described in these studies, to identify host factors present in abscessed tissue, Imaging Mass Spectrometry (IMS) was applied to a mouse model of staphylococcal infection. IMS utilizes matrix-assisted laser desorption ionization time-of-flight MS (MALDI-TOF-MS) to profile and map the distribution of proteins present in thin tissue sections (2). This technology determines relative protein concentrations across intact tissue, simultaneously imaging at hundreds of distinct molecular weights. IMS thus provides information on the spatial distribution of individual proteins in vivo without the need for antibodies, allowing an unbiased analysis of protein distribution in healthy and diseased animals (2-4). The staphylococcal abscess is an anatomical site exhibiting macroscopic differences from healthy tissue, making it amenable to IMS-based protein detection. This work represents the first application of IMS to host-microbe interactions.

To analyze protein distribution in abscesses from *S. aureus*-infected mice, 6-8 week old female C57BL/6 mice were either not exposed to staphylococci (uninfected), infected with $1 \times 10^5$ CFU of *S. aureus* (low dose; does not lead to abscesses formation), or infected with $1 \times 10^6$ CFU of *S.*

*aureus* (high dose; leads to significant kidney and liver abscess formation). Kidneys from uninfected and infected animals were sectioned, coated with sinapinic acid, and analyzed using IMS. Representative images from these analyses are shown in FIG. 1A. FIG. 1A includes mass spectrometric images of *S. aureus* infected and uninfected murine kidneys. Optical images of three frozen kidney sections mounted on a gold-coated MALDI plate is shown in the far left column. Two-dimensional ion density map of representative proteins expressed in infected or uninfected murine tissue is shown in the four right panels with mass-to-charge values (m/z) for each distinct protein shown at the bottom of the panels. The ion density map is illustrated as a pseudo-color image. The presented images represent a subset of approximately 150 protein images obtained in these analyses. Among the proteins present exclusively in abscessed tissue was a protein exhibiting m/z of 10,165 that displayed the strongest mass-to-charge signal observed in these experiments (FIG. 1A). The considerable abundance of an approximately 10 kDa protein specifically in *S. aureus*-induced murine abscesses implies a contribution of this protein to the host-pathogen interaction.

To identify this approximately 10 kDa protein, abscessed or corresponding healthy tissue was dissected from *S. aureus*-infected murine kidneys. Proteins were extracted using 50% acetonitrile and 0.2% trifluoroacetic acid and were subsequently separated using 1-dimensional SDS-PAGE. FIG. 1B includes SDS-PAGE analysis of material extracted from kidneys of uninfected (lane 1) or infected (lane 2) mice followed by MS/MS-based identification of proteins. As illustrated in FIG. 1B, the analysis revealed significant alterations in protein expression between infected and uninfected tissue. A colloidal blue stained protein band present exclusively in the abscessed tissue corresponding to a predicted size of approximately 10 kDa was excised from the gel, digested with trypsin, and analyzed using LC-MS/MS. These analyses revealed that the band present in the excised gel slice contained trypsin peptide cleavage fragments that match S100A8, a component of the calprotectin heterodimer (S100A8/S100A9) (5).

With reference to FIG. 1C, immunohistochemistry using anti-S100A8 antisera as a probe revealed robust immune cell recruitment to staphylococcal abscesses highlighted by a prominent polymorphonuclear leukocyte population (arrowhead denotes abscess). Moreover, S100A8 is only detectable in tissue from infected mice and localizes coordinately with the sites of staphylococcal abscesses. Furthermore, with reference to FIG. 1D, IMS revealed S100A8 and S100A9 co-localize to the staphylococcal abscesses, supporting heterodimeric calprotectin as the functional form of these proteins inside tissue abscesses. FIG. 1D includes mass spectrometric images of *S. aureus* infected and uninfected murine kidneys showing the distribution of S100A8 (m/z 10,165) and S100A9 (m/z 12,976) (arrowheads denote abscesses).

FIGS. 2A-2F include histological analyses of kidney tissue sections harvested from uninfected or infected mice 96 hr post-infection. Kidney sections from (FIG. 2A) uninfected and (FIG. 2B) infected C57BL/6 mice were stained with hematoxylin and eosin to assess inflammation. FIGS. 2C-2F include representative sections of tissue from uninfected or infected mice immunostained for S100A8. The arrowhead in FIG. 2D denotes abscess formation. The arrowhead in FIG. 2F denotes individual cell staining positive for S100A8. P.A. stands for proximal to the abscess, and I.A. stands for inside the abscess.

Calprotectin is an S100 EF-hand $Ca^{2+}$ binding protein that accounts for approximately 40% of the cytosolic protein pool of neutrophils (5), and is a minor cytoplasmic constituent of monocytes, macrophages, and keratinocytes (6-8). Approximately twenty years ago calprotectin was first shown to inhibit the growth of a variety of fungal and bacterial pathogens in vitro (9), however a mechanistic explanation for this antimicrobial activity has yet to be formulated. Calprotectin's antimicrobial activity has been proposed to be due to calprotectin-mediated chelation of nutrient $Zn^{2+}$. This hypothesis is largely based on the fact that S100A8 and S100A9 encode $Zn^{2+}$ binding His-X-X-X-His motifs (10), and the finding that the antimicrobial activity of calprotectin against *Candida albicans* and *Borrelia burgdorferi* can be overcome by the addition of excess $Zn^{2+}$ (11, 12). However, it has not been established that microbial pathogens exposed to calprotectin are $Zn^{2+}$ starved. In addition, *C. albicans* and *B. burgdorferi* have high nutrient $Zn^{2+}$ requirements, making them unusually sensitive to $Zn^{2+}$ deprivation (13, 14). Moreover, it has been speculated that the $Zn^{2+}$-reversibility of calprotectin's candidastatic and bacteriostatic effects may be due to $Zn^{2+}$-dependent conformational changes in the protein and not direct sequestration of this nutrient (15). Thus, the considerable body of data on the antimicrobial mechanism of calprotectin is largely indirect and the contribution of calprotectin to the host-pathogen interaction has not been evaluated.

Figure 3:
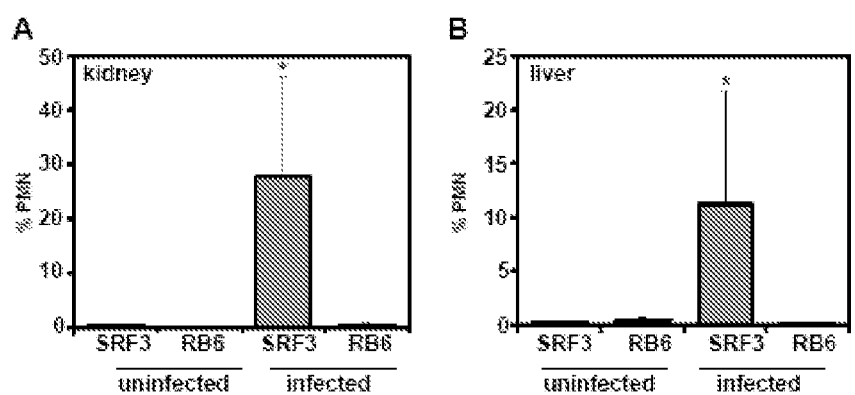
FIGS. 3A and 3B are bar graphs depicting the results of flow cytometry analysis of neutrophils in kidney and liver tissue, respectively, of uninfected or S. aureus-infected murine tissue 96 hr post-infection.

The first step in the approach described herein was to ascertain the cell population responsible for recruitment and/or expression of S100A8 in the staphylococcal abscess by infecting wild-type and neutropenic mice with *S. aureus* and applying IMS across the kidneys and livers of infected animals. To this end, mice were initially depleted of neutrophils by administering the rat IgG2b α-Gr-1 monoclonal antibody RB6-8C5 (FIG. 3) and infected with a dose of *S. aureus* that induces lesion formation without leading to lethality (FIGS. 3A and 3B). FIGS. 3A and 3B include results of a flow cytometry analysis of neutrophils in kidney and liver tissue of uninfected or *S. aureus* infected murine tissue 96 hr post-infection. Plots are gated on live cells with large and granular forward and side scatter properties. Data represent the mean+/−the standard deviation of quadruplicate experiments. *, $P<0.001$.

Figure 4:
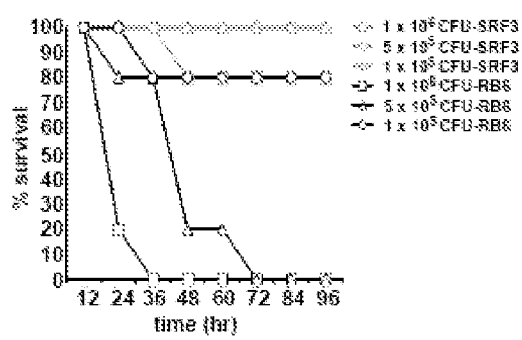
FIG. 4 is a survival curve of neutrophil-replete mice exposed to various doses of S. aureus.

FIG. 4 includes a survival curve of neutrophil-replete mice exposed to various doses of *S. aureus*. Six to eight week old female C57/BL6 mice were infected with *S. aureus* at the listed doses. Prior to infection, mice were either treated with an anti-neutrophil antibody (RB6) to deplete neutrophils, or an isotype matched antibody (SRF3). Infected animals were followed for 96 hours and survival was recorded. RB6-treated mice infected with $1\times10^5$ CFU typically survived in spite of lesion formation in various organs.

With reference to FIG. 1E, results from an imaging mass spectrometry analyses of S100A8 expression within kidneys and livers from neutrophil replete uninfected mice (lane 1), neutrophil replete infected mice (lane 2), neutrophil-depleted uninfected mice (lane 3), and neutrophil-depleted infected mice (lane 4) are shown. The top row in each organ set shows matrix treated organs, and the bottom row in each organ set shows IMS. Asterisks denote sites of abscess formation. Neutrophils were depleted by administering the mAb RB6. An isotype matched mAb SRF3 was used as a control in neutrophil replete mice. IMS revealed that S100A8 localizes coordinately with staphylococcal kidney and liver abscesses in neutrophil replete mice. In contrast, infected neutropenic mice do not express S100A8 in the kidney or liver in spite of *S. aureus*-induced lesion formation in these organs. These findings indicate that the presence of S100A8 in infected kidney and liver abscesses is dependent on an intact neutrophil compartment.

Figure 5:
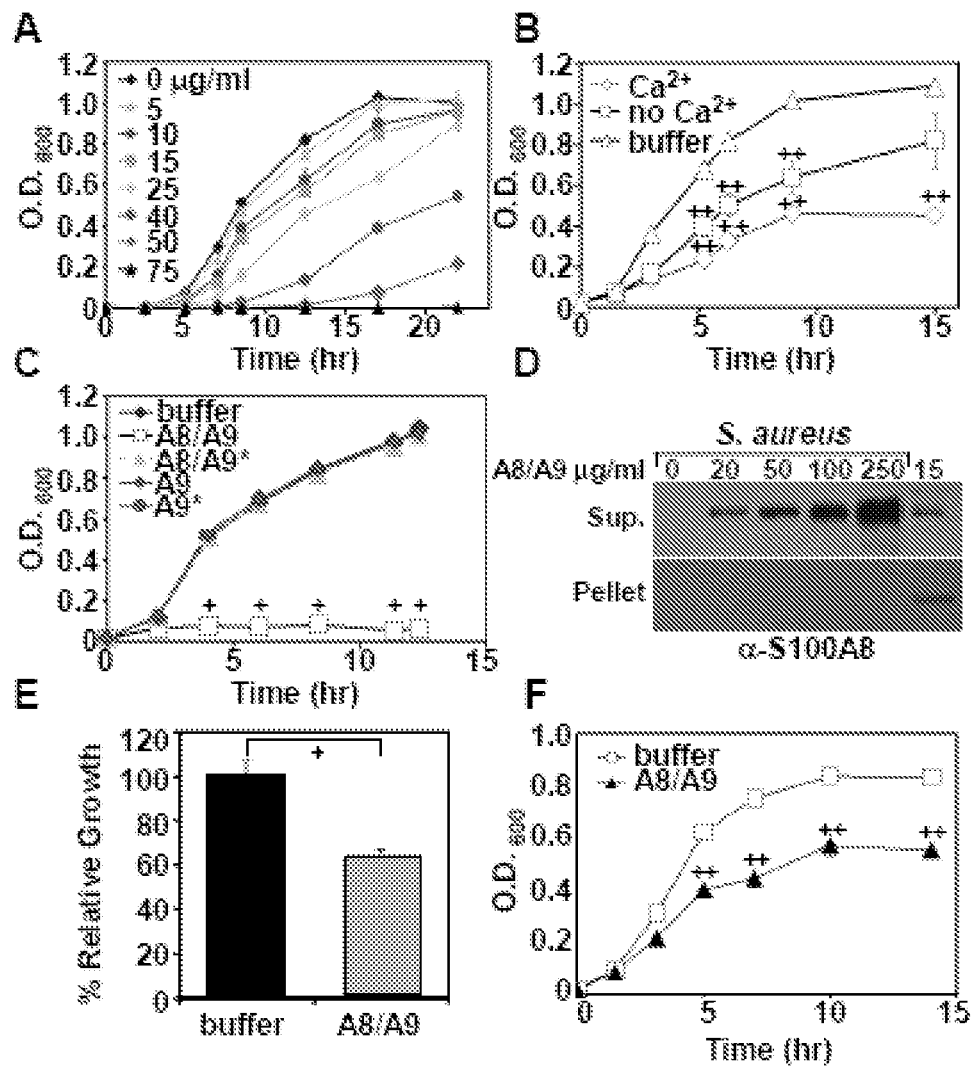
FIG. 5A is a graph illustrating the effect of recombinant calprotectin on S. aureus growth in vitro as a function of time.
FIG. 5B is a graph showing S. aureus growth as a function of time in the presence of calprotectin purified with ($Ca^{2+}$) or without calcium (no $Ca^{2+}$) as compared to buffer alone (buffer).
FIG. 5C is a graph showing S. aureus growth as a function of time in the presence of S100A8/A9 heterodimers (A8/A9), S100A9 homodimers (A9), S100A8/S100A9C3 S heterodimers (A8/A9*), or S100A9C3S homodimers (A9*) as compared to buffer alone (buffer).
FIG. 5D includes the results of an immunoblot assay assessing calprotectin's ability to bind staphylococcal cells using an S100A8-specific antibody; in lanes 1-5 S. aureus were mixed with increasing concentrations of calprotectin, and calprotectin (15 µg/ml) was used as a control marker in lane 6.
FIG. 5E is a bar graph illustrating the ability of calprotectin (A8/A9) to inhibit S. aureus growth across a dialysis membrane as compared to buffer alone (buffer).
FIG. 5F is a graph showing growth kinetics of S. aureus in chemically defined media that were pre-treated with calprotectin (A8/A9) or buffer control (buffer) and filtered using a centricon column with a 5 kD cutoff.

S100A8 and S100A9 were co-purified to form functional calprotectin heterodimers using published protocols (16). FIG. 5A illustrates the effect of recombinant calprotectin on *S. aureus* growth in vitro. It was found that calprotectin inhibits *S. aureus* growth in a dose-dependent manner with complete growth arrest observed at 75 μg/ml calprotectin. These concentrations are physiologically relevant considering the estimated concentration of calprotectin in the neutrophil cytoplasm is approximately 15 mg/ml, and greater than 1 mg/ml of calprotectin is detectable in abscess fluid of patients (17-19).

FIG. 5B depicts *S. aureus* growth in the presence of calprotectin purified with ($Ca^{2+}$) or without calcium (no $Ca^{2+}$) as compared to buffer alone (buffer). The anti-staphylococcal activity of calprotectin is augmented when the protein is purified in the presence of $Ca^{2+}$. This result is consistent with calprotectin's assignment as an S100 EF-hand $Ca^{2+}$ binding protein, and the in vitro observation that $Ca^{2+}$ promotes calprotectin heterotetramerization and subsequent configuration of high affinity $Zn^{2+}$ binding sites (20).

Although S100A9 preferentially forms heterodimers in vitro and in vivo (16), it can be expressed independently from S100A8 suggesting that homodimers retain some level of functionality (21, 22). To determine whether heterodimer formation is essential for calprotectin to inhibit staphylococcal growth, the sensitivity of *S. aureus* to the S100A9 homodimer was tested. FIG. 5C includes an analysis of *S. aureus* growth in the presence of S100A8/A9 heterodimers (A8/A9), S100A9 homodimers (A9), S100A8/S100A9C3S heterodimers (A8/A9*), or S100A9C3S homodimers (A9*) as compared to buffer alone (buffer). It was found that the S100A9 homodimer is unable to inhibit *S. aureus* growth at concentrations ranging from 5-500 μg/ml. The instability of S100A8 homodimers (16) precluded investigation of its activity in these assays. S100A9 contains a cysteine residue at amino acid position 3 that has been suggested to play a role in the functionality of calprotectin heterodimers (16). This supposition was tested by assaying the anti-staphylococcal properties of a previously described cysteine-to-serine mutant (S100A9C3S) (16). Neither S100A9C3S homodimer nor S100A8/S100A9C3S heterodimer were able to inhibit staphylococcal growth (FIG. 5C). Taken together, these findings indicate that heterodimerization, $Ca^{2+}$ binding, and the cysteine residue at position 3 in S100A9 contribute to calprotectin's ability to inhibit bacterial growth.

With reference to FIG. 5D, calprotectin's ability to bind staphylococcal cells was assessed. *S. aureus* was incubated with calprotectin, centrifuged, washed, and whole cell lysates immunoblotted with an S100A8 specific antibody. In lanes 1-5 *S. aureus* were mixed with increasing concentrations of calprotectin. Calprotectin (15 μg/ml) was used as a control marker in lane 6. The antimicrobial activity of calprotectin is proposed to occur through metal ion chelation, suggesting that physical contact between calprotectin and *S. aureus* is not required for growth inhibition. Consistent with this, calprotectin-staphylococci interactions using a co-precipitation assay could not be detected, as shown in FIG. 5D.

With reference to FIG. 5E, to assess further whether calprotectin requires physical contact to mediate growth inhibition, *S. aureus* was grown in medium containing calprotectin (A8/A9) but physically separated by a dialysis membrane, and compared to buffer alone (buffer). It was found that staphylococcal growth was reduced approximately 40% by calprotectin (500 μg/ml) in the absence of physical contact.

Bacterial growth medium was then treated with calprotectin followed by its removal through filtration, and the ability of *S. aureus* to grow in this calprotectin-treated medium was measured. Successful removal of calprotectin from the treated medium was confirmed by immunoblot using anti-S100A8 antisera (data not shown). With reference to FIG. 5F, *S. aureus* growth was reduced in medium that had been transiently treated with calprotectin (A8/A9) as compared to medium treated with buffer alone (buffer). These data are consistent with a model whereby calprotectin inhibits *S. aureus* growth through the sequestration of an essential growth factor from the medium.

Figure 6:
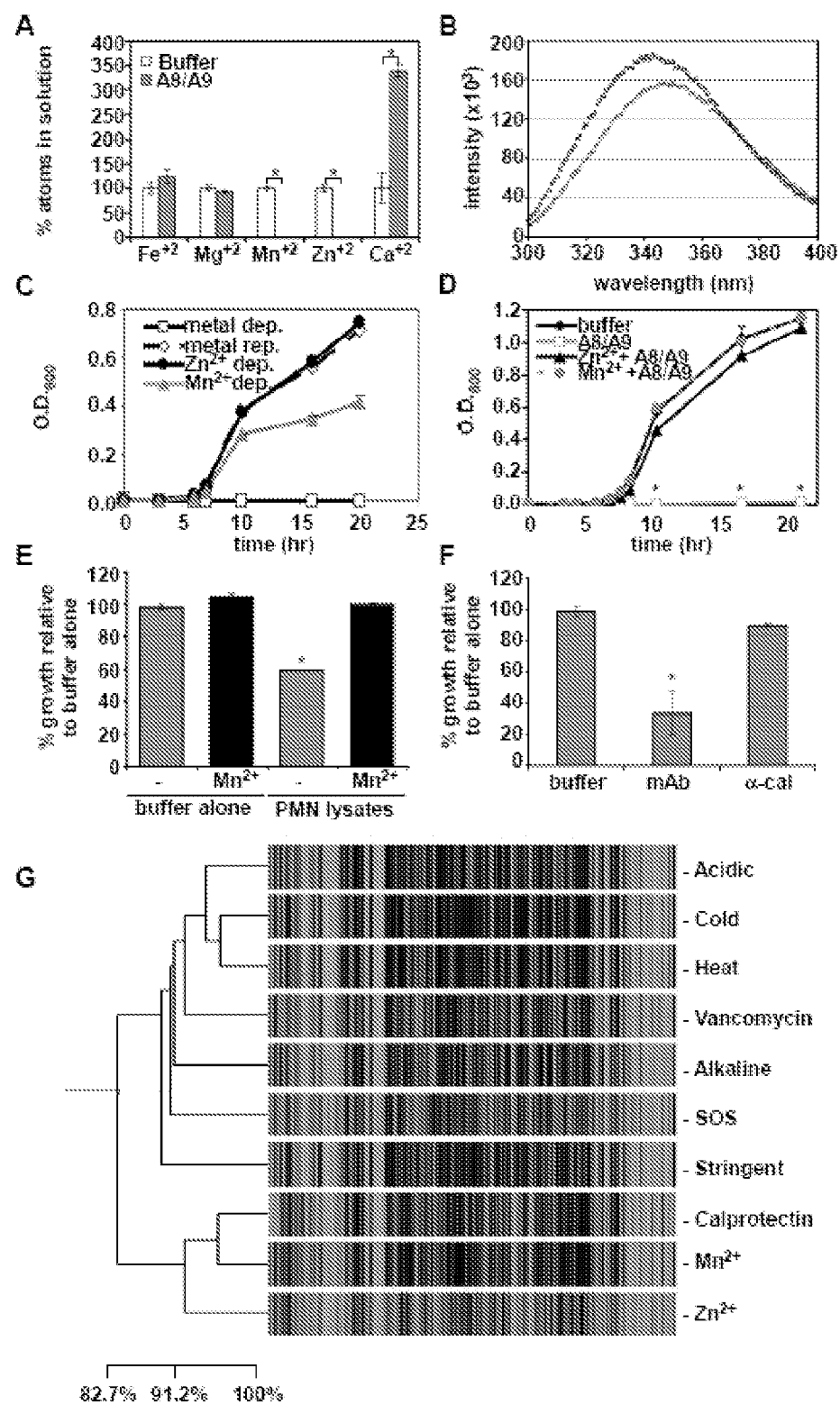
FIG. 6A is a graph illustrating the results of an ICP-MS analyses of metals in chemically defined media following exposure to calprotectin (A8/A9).
FIG. 6B is a fluorescence emission spectra of S100A8/S100A9 in the absence (diamonds) and presence (squares) of $Mn^{2+}$ (250 µM).
FIG. 6C is a graph illustrating the sensitivity of S. aureus to growth in media lacking all cations (metal dep.), lacking $Zn^{2+}$ ($Zn^{2+}$ dep), or lacking $Mn^{2+}$ ($Mn^{2+}$ dep).
FIG. 6D is a graph illustrating the effect of calprotectin (A8/A9) on S. aureus growth in the presence of excess Zn or Mn calprotectin (A8/A9) or buffer alone (buffer).
FIG. 6E is a bar graph showing the growth of S. aureus upon exposure to PMN lysates in the presence or absence of excess $Mn^{2+}$ as compared to buffer alone.
FIG. 6F is a bar graph showing the growth of S. aureus upon exposure to PMN lysates that have been immunodepleted of calprotectin (α-cal), treated with a non-specific control antibody (mAb), or treated with buffer control (buffer).
FIG. 6G includes the results of a hierarchical clustering analysis, illustrating the relatedness of transcription profiles of S. aureus cells subjected to indicated stresses.

To determine whether calprotectin chelates nutrient cations, purified calprotectin was incubated with growth medium containing known concentrations of $Fe^{2+}$, $Mn^{2+}$, $Mg^{2+}$, $Ca^{2+}$, and $Zn^{2+}$. Calprotectin was subsequently removed by filtration, and the $Fe^{2+}$, $Mn^{2+}$, $Mg^{2+}$, $Ca^{2+}$, and $Zn^{2+}$ levels were determined by Inductively Coupled Plasma-Mass Spectrometry (ICP-MS). These analyses revealed no statistical difference in the number of $Fe^{2+}$ or $Mg^{2+}$ atoms remaining in the medium upon transient treatment with calprotectin (FIG. 6A). In contrast, $Mn^{2+}$ and $Zn^{2+}$ were not detected following calprotectin treatment (FIG. 6A), demonstrating that calprotectin chelates nutrient $Mn^{2+}$ and $Zn^{2+}$ from staphylococcal growth medium. A significant increase in detectable $Ca^{2+}$ in the growth medium following calprotectin treatment is likely due to the release of excess $Ca^{2+}$ ions bound to calprotectin in secondary binding sites as a by-product of purification in a $Ca^{2+}$-rich buffer. The data described herein represent the first indication of a role for calprotectin in binding $Mn^{2+}$.

In order to validate this hypothesis, the $Mn^{2+}$-binding properties of calprotectin were examined using a standard fluorescence spectroscopy assay. FIG. 6B includes fluorescence emission spectra of S100A8/S100A9 in the absence (diamonds) and presence (squares) of $Mn^{2+}$ (250 μM). The shift in the intensity of wavelength of the peak maximum as a result of addition of $Mn^{2+}$, confirmed that calprotectin does bind this metal ion.

To determine the sensitivity of *S. aureus* to $Zn^{2+}$ and $Mn^{2+}$ starvation, *S. aureus* was grown in media deplete in all cations (metal dep.), deplete in $Zn^{2+}$ ($Zn^{2+}$ dep.), and deplete in $Mn^{2+}$ ($Mn^{2+}$ dep.). With reference to FIG. 6C, these experiments revealed that *S. aureus* is acutely sensitive to $Mn^{2+}$ deprivation, whereas the bacteria proliferate in media that is virtually devoid of detectable $Zn^{2+}$.

With reference to FIG. 6D, addition of excess $Mn^{2+}$ and $Zn^{2+}$ to growth medium rescues calprotectin-mediated inhibition of staphylococcal proliferation, confirming that $Mn^{2+}$ and $Zn^{2+}$ chelation is responsible for the anti-staphylococcal activity of calprotectin. Presumably, the ability of individual metals to rescue staphylococcal growth is due to saturation of the $Zn^{2+}/Mn^{2+}$ binding sites of calprotectin by either excess $Zn^{2+}$ or $Mn^{2+}$.

Figure 7:
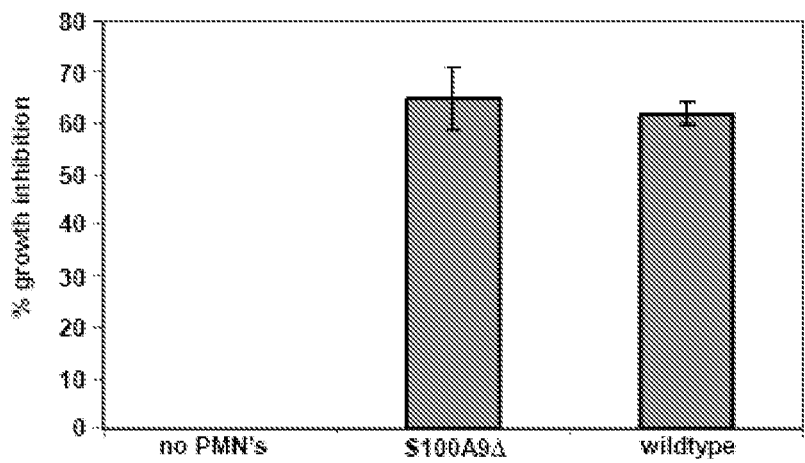
FIG. 7 is a bar graph showing the growth inhibition of S. aureus in response to exposure to peritoneal PMNs extracted from wildtype and S100A9Δ mice.

The contribution of calprotectin to neutrophil-mediated bacterial killing was determined. Neutrophils (peritoneal PMNs) were extracted from wildtype and calprotectin-deficient mice (S100A9Δ) mice and incubated in vitro with *S. aureus* to measure phagocytic-dependent killing. With reference to FIG. 7, neutrophils extracted from wildtype and calprotectin-deficient mice kill *S. aureus* in vitro with similar efficiency suggesting that calprotectin does not contribute to phagocytic killing. Data are presented as percent of bacteria that were killed after two hours of exposure to PMNs.

Next, we extracted the cytoplasmic compartment from purified neutrophils and measured its antimicrobial activity. Due to the low yield of cytoplasmic material from murine neutrophil extractions, these experiments were performed using neutrophils extracted from human blood. With reference to FIGS. 6E and 6F, these experiments revealed that the cytoplasmic fraction of neutrophils is capable of inhibiting staphylococcal growth and this activity is reversible upon the addition of excess $Mn^{2+}$ or immunodepletion of calprotectin.

Figure 8:
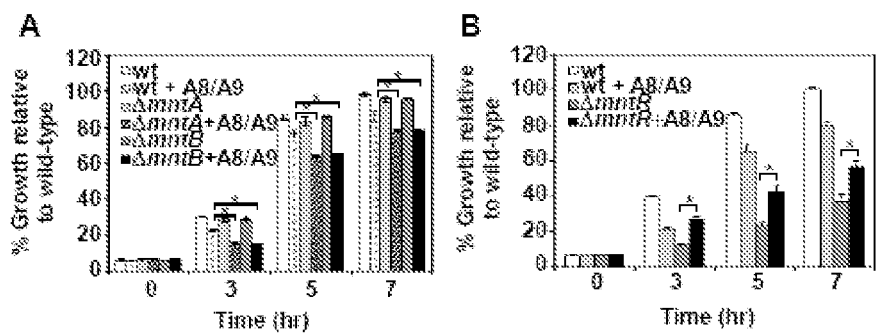
FIG. 8A is a graph illustrating the bacteriostatic effect of calprotectin against ΔmntA and ΔmntB in $Mn^{2+}$ replete media.
FIG. 8B is a graph illustrating the bacteriostatic effect of calprotectin against either ΔmntR in the presence of toxic levels of $Mn^{2+}$.

As a further demonstration that *S. aureus* exposed to calprotectin are $Mn^{2+}$-starved, *S. aureus* strains were created that are inactivated for the $Mn^{2+}$-dependent transcriptional repressor (ΔmntR), or the $Mn^{2+}$ uptake system (ΔmntA, ΔmntB). MntR is a repressor of the MntABC transport system responsible for $Mn^{2+}$ acquisition, and its disruption renders *S. aureus* acutely sensitive to $Mn^{2+}$-mediated toxicity (23). It was reasoned that if calprotectin efficiently chelates nutrient $Mn^{2+}$, then the addition of calprotectin to medium supplemented with toxic levels of $Mn^{2+}$ should protect ΔmntR from Mn-toxicity. Conversely, it was predicted that strains defective in MntABC should be more sensitive to calprotectin-dependent toxicity due to an inability to compete for available $Mn^{2+}$. With reference to FIGS. 8A and 8B, the bacteriostatic effect of calprotectin was determined against either (FIG. 8A) ΔmntA and ΔmntB in $Mn^{2+}$ replete media or (FIG. 8B) ΔmntR in the presence of toxic levels of $Mn^{2+}$. It was found that co-incubation with calprotectin alleviates the sensitivity of ΔmntR to excess $Mn^{2+}$, while strains defective in mntA or mntB are more sensitive to calprotectin toxicity.

Bacteria respond to alterations in metal concentrations through changes in gene expression. These changes are metal-specific and hence represent expression signatures that can be used to determine the environmental stress placed on a bacterial population (24). Therefore, if calprotectin chelates nutrient $Zn^{2+}$ and $Mn^{2+}$, exposing *S. aureus* to calprotectin should elicit a gene expression profile consistent with $Zn^{2+}$ and $Mn^{2+}$ starvation. Since the $Zn^{2+}$ and $Mn^{2+}$ regulons of *S. aureus* have not been reported, the staphylococcal transcripts that change expression upon $Zn^{2+}$ or $Mn^{2+}$ starvation were first determined using *S. aureus* Affymetrix GENECHIP®. *S. aureus* decreased the expression of 104 genes and increased the expression of 9 genes upon $Zn^{2+}$ starvation (Supplemental Table 1-2). By comparison, *S. aureus* grown in $Mn^{2+}$ deplete conditions exhibited less pronounced changes in gene expression highlighted by the down-regulation of 12 genes and the up-regulation of 2 genes (Supplemental Table 3-4).

Supplemental Table 1: *S. aureus* transcripts decreased in the absence of $Zn^{2+}$

| Locus[a] | Common name[c] | Fold induction | Description[d] |
|---|---|---|---|
| SA0150 | cap5 | 2.5 | capsular polysaccharide biosynthesis |
| SA0222 | ldh | 3.8 | lactate/malate dehydrogenase |
| SA0253 | rbsK | 2.6[b] | carbohydrate kinase |
| SA0594 | tagG | 2.2 | teichoic acid permease |
| SA0743 | bacA | 2.2 | bacitracin resistance protein |
| SA0823 | uvrB | 3.6 | helicase |
| SA0846 | rnr | 2.4 | ribonuclease II |
| SA1028 | htrA | 2.6 | peptidase S1, chymotrypsin |
| SA1062 | atl | 4.5 | autolysin |
| SA1095 | cydB | 3.6 | cytochrome d ubiquinol oxidase |
| SA1397 | msrA | 3.7 | peptide methionine sulfoxide reductase |
| SA1401 | tyrA | 2.9 | pephenate dehydrogenase |
| SA1450 | arlS | 3.3 | histidine kinase |
| SA1451 | arlR | 3.2 | response regulator |
| SA1734 | gapA | 3.6[b] | glyceraldehyde 3-phosphate dehydrogenase |
| SA1739 | phoR | 3.1 | histidine kinase |
| SA1871 | epiG | 2.5[b] | epidermin immunity protein F |
| SA2025 | agrC | 3.9 | accessory gene regulator protein C |
| SA2137 | czrA | 2.3 | transcriptional regulator |
| SA2165 | htsC | 2.8 | heme transport system permease |
| SA2350 | tcaB | 3.4[b] | general substrate transporter |
| SA2514 | gntP | 2.2[b] | gluconate transporter |
| SA2534 | frp | 2.5 | nitroreductase |
| SA2539 | srtA | 2.9 | sortase |
| SA2562 | ogt | 3.0 | methylguanine DNA methyltransferasese |
| SA2577 | crtM | 2.4[b] | dehydrosqualene synthase |
| SA2627 | betA | 24.2[b] | choline dehydrogenase |
| SA2628 | betB | 16.5[b] | betaine aldehyde dehydrogenase |
| SA2632 | cudT | 9.6 | osmoprotectant transporter |
| SA2635 | nrdD | 2.7[b] | formate C-acetyltransferase glycine radical |
| SA2639 | cyst | 2.2 | sulfite reductase |
| SA0013 | NA | 3.1 | conserved hypothetical protein |
| SA0166 | NA | 2.0[b] | conserved hypothetical protein |
| SA0202 | NA | 3.5[b] | sensor histidine kinase family protein |
| SA0220 | NA | 5.3[b] | putative flavohemoprotein |
| SA0257 | NA | 2.7[b] | putative ribose operon repressor |
| SA0262 | NA | 2.4 | choloylglycine hydrolase family protein |
| SA0314 | NA | 2.8 | conserved hypothetical protein |
| SA0444 | NA | 2.2 | conserved hypothetical protein |
| SA0454 | NA | 3.5[b] | sodium:dicarboxylate symporter family |
| SA0456 | NA | 3.1 | conserved hypothetical protein |
| SA0487 | NA | 3.1 | conserved hypothetical protein |
| SA0507 | NA | 4.3 | LysM domain protein |
| SA0602 | NA | 2.0 | hydrolase, haloacid dehalogenase-like family |
| SA0647 | NA | 3.4[b] | conserved hypothetical protein |
| SA0665 | NA | 2.8 | putative iron binding protein |
| SA0717 | NA | 2.3 | sensor histidine kinase |
| SA0737 | NA | 4.5 | conserved hypothetical protein |
| SA0741 | NA | 2.8 | conserved hypothetical protein |
| SA0742 | NA | 3.3 | conserved hypothetical protein |
| SA0764 | NA | 3.5 | glycosyl transferase, group 2 family protein |
| SA0788 | NA | 3.7 | oligopeptide transporter family protein |
| SA0808 | NA | 2.8 | conserved hypothetical protein |
| SA0831 | NA | 2.3 | conserved hypothetical protein |
| SA0868 | NA | 2.6[b] | conserved hypothetical protein |
| SA0870 | NA | 2.8 | putative LysE family transporter |
| SA0958 | NA | 2.8 | putative RNA binding S1 |
| SA0959 | NA | 2.3 | flavin oxidoreductase family |
| SA1043 | NA | 3.4 | glycosyl transferase, group 1 family protein |
| SA1044 | NA | 2.1 | conserved hypothetical protein |
| SA1096 | NA | 3.8 | TrkA potassium uptake family protein |
| SA1116 | NA | 2.5 | inositol monophosphatase family protein |
| SA1252 | NA | 3.7 | putative acetyltransferase |
| SA1259 | NA | 3.4 | conserved hypothetical protein |
| SA1357 | NA | 3.7[b] | thermonuclease precursor family protein |
| SA1358 | NA | 2.7 | conserved hypothetical protein |
| SA1380 | NA | 3.2 | conserved hypothetical protein |
| SA1395 | NA | 2.3 | conserved hypothetical protein |
| SA1413 | NA | 2.4 | conserved hypothetical protein |
| SA1414 | NA | 2.7 | ABC transporter |
| SA1468 | NA | 2.8[b] | conserved hypothetical protein |
| SA1471 | NA | 2.4 | putative cell wall enzyme EbsB |
| SA1481 | NA | 7.1[b] | conserved hypothetical protein |
| SA1485 | NA | 3.3 | conserved hypothetical protein |
| SA1486 | NA | 2.6 | conserved hypothetical protein |
| SA1530 | NA | 2.3 | Xaa-Pro dipeptidase homolog |
| SA1543 | NA | 2.0 | oxidoreductase, aldo/keto reductase family |
| SA1588 | NA | 2.7 | proline dipeptidase |
| SA1703 | NA | 2.2 | putative rod shape-determining protein |
| SA1713 | NA | 3.5 | hypothetical protein |
| SA1788 | NA | 3.5 | conserved hypothetical protein |

Supplemental Table 1: *S. aureus* transcripts decreased in the absence of $Zn^{2+}$

| Locus[a] | Common name[c] | Fold induction | Description[d] |
|---|---|---|---|
| SA1796 | NA | 2.4 | conserved hypothetical protein |
| SA1796 | NA | 2.2 | conserved hypothetical protein |
| SA1835 | NA | 2.9 | oxidoreductase, aldo/keto reductase family |
| SA1840 | NA | 2.4 | conserved hypothetical protein |
| SA1903 | NA | 2.1 | conserved hypothetical protein |
| SA1934 | NA | 2.5 | conserved hypothetical protein |
| SA1939 | NA | 2.2 | phosphotyrosine protein phosphatase |
| SA1941 | NA | 3.4 | putative ribonuclease BN |
| SA2004 | NA | 2.6 | leukocidin F subunit |
| SA2006 | NA | 3.3 | aerolysin/leukocidin family protein |
| SA2007 | NA | 5.6 | peptidase, M20/M25/M40 family |
| SA2037 | NA | 2.8 | similar to DNA mismatch repair protein |
| SA2136 | NA | 3.8 | conserved hypothetical protein |
| SA2143 | NA | 2.1 | conserved hypothetical protein |
| SA2148 | NA | 2.1 | PTS system, mannitol-specific IIA component |
| SA2167 | NA | 2.7 | similar to ferrichrome ABC transporter |
| SA2189 | NA | 2.3 | transcriptional regulator, Sir2 family |
| SA2192 | NA | 2.1 | conserved hypothetical protein |
| SA2278 | NA | 2.1 | acyl-CoA dehydrogenase-related protein |
| SA2299 | NA | 2.0[b] | conserved hypothetical protein |
| SA2306 | NA | 2.4 | abortive infection protein family |
| SA2364 | NA | 2.7 | conserved hypothetical protein |
| SA2374 | NA | 4.2[b] | conserved hypothetical protein |
| SA2383 | NA | 3.0 | conserved hypothetical protein |
| SA2404 | NA | 2.1 | conserved hypothetical protein |
| SA2405 | NA | 2.2 | conserved hypothetical protein |
| SA2407 | NA | 6.8 | conserved hypothetical protein |
| SA2412 | NA | 2.8 | amino acid ABC transporter |
| SA2433 | NA | 3.6 | conserved hypothetical protein |
| SA2442 | NA | 3.6 | Na+/H+ antiporter, putative |
| SA2443 | NA | 2.2 | conserved hypothetical protein |
| SA2459 | NA | 3.1 | carboxylesterase |
| SA2487 | NA | 2.9[b] | conserved hypothetical protein |
| SA2491 | NA | 6.7 | conserved hypothetical protein |
| SA2493 | NA | 3.9[b] | conserved hypothetical protein |
| SA2597 | NA | 2.1 | hydrolase, alpha/beta hydrolase fold family |
| SA2607 | NA | 2.1 | hypothetical protein |
| SA2610 | NA | 3.0 | putative transcriptional regulator, TetR family |
| SA2631 | NA | 10.7[b] | beta-lactamase-like |
| SA2666 | NA | 2.6 | N-acetylmuramoyl-L-alanine amidase |
| SA2727 | NA | 3.2 | integrase/recombinase, core domain family |
| SAS1634 | NA | 2.3 | putative beta-lactamase family protein |

[a]*S. aureus* strain COL locus, unless otherwise indicated (strain preceeds locus identifier).
[b]transcript was below the lower limits of sensitivity in unstressed cells, the amount of change represents an estimate.
[c]NA = Not available
[d]description of predicted function Supplemental Table 2: *S. aureus* transcripts increased in the absence of $Zn^{2+}$

| Locus[a] | Common name[c] | Fold induction | Description[d] |
|---|---|---|---|
| SA0387 | NA | 3.1 | exotoxin 11 |
| SA0469 | NA | 2.6 | exotoxin 1, putative |
| SA1037 | NA | 4.3 | conserved hypothetical protein |
| SA1166 | NA | 3.1 | hypothetical protein |
| SA1178 | NA | 3.5 | exotoxin 1, putative |
| SA1179 | NA | 2.5 | exotoxin 4, putative |
| SA1180 | NA | 3.1 | exotoxin 3, putative |
| SA2357 | NA | 5.8[b] | ABC transporter, permease protein |
| SAS0388 | NA | 3.8 | exotoxin 3 |

[a]*S. aureus* strain COL locus, unless otherwise indicated (strain preceeds locus identifier).
[b]transcript was below the lower limits of sensitivity in unstressed cells, and thus the amount of change represents an estimate.
[c]NA = Not available
[d]description of predicted function Supplemental Table 3: *S. aureus* transcripts decreased in the absence of $Mn^{2+}$

| Locus[a] | Common name | Fold induction | Description[c] |
|---|---|---|---|
| SA1062 | atl | 2.3 | bifunctional autolysin |
| SA2627 | betA | 2.3 | choline dehydrogenase |
| SA2628 | betB | 2.1 | betaine aldehyde dehydrogenase |
| SA2632 | cudT | 2.2 | osmoprotectant transporter, BCCT family |
| SA2421 | hlgC | 3.8[b] | gamma hemolysin, component C |
| SA2149 | mtlD | 2.1 | mannitol-1-phosphate 5-dehydrogenase |
| SA0787 | NA | 2.4 | conserved hypothetical protein |
| SA2007 | NA | 2.9 | peptidase |
| SA2088 | NA | 2.8 | putative sceD protein |
| SA2176 | NA | 4.3 | osmoprotectant transporter, BCCT family |
| SA2416 | NA | 2.6 | similar to cation efflux family protein |
| SAV0890 | NA | 3.8 | phi Mu50B-like protein |
| SAV0896 | NA | 4.4[b] | phi Mu50B-like protein |
| SAV0910 | NA | 3.8[b] | tail fiber |

[a]*S. aureus* strain COL locus, unless otherwise indicated (strain preceeds locus identifier).
[b]transcript was below the lower limits of sensitivity in unstressed cells, and thus the amount of change represents an estimate.
[c]NA = Not available.
[d]description of predicted function.

Supplemental Table 4: *S. aureus* transcripts increased in the absence of $Mn^{2+}$

| Locus[a] | Common name | Fold induction | Description[c] |
|---|---|---|---|
| SA1166 | NA | 2.0 | hypothetical protein |
| SA0910 | NA | 2.2 | similar to quinol oxidase polypeptide IV QoxD |

[a]*S. aureus* strain COL locus, unless otherwise indicated (strain preceeds locus identifier).
[b]NA = Not available
[c]description of predicted function Transcriptome analyses of *S. aureus* grown in the presence of a sub-inhibitory concentration of calprotectin revealed 61 transcripts that change abundance (Supplemental Table 5-6). Although calprotectin treatment increased the expression of 30 genes, the large majority of these genes do not have ascribed functions (Supplemental Table 5). In contrast, calprotectin treatment decreased the expression of a variety of genes with predicted roles in metal metabolism and pathogenesis (Supplemental Table 6). More specifically, calprotectin treatment led to the down-regulation of a similar subset of genes to those that are down-regulated upon $Zn^{2+}$ and $Mn^{2+}$ starvation (Supplemental Table 5).

Supplemental Table 5: *S. aureus* transcripts increased in the presence of calprotectin or zinc-deplete growth conditions

| Locus[a] | Common name | Fold induction calprotectin | Fold induction $Zn^{2+}$ deplete | Description[c] |
|---|---|---|---|---|
| SA1329 | femC | 2.7 | 0.6 | glutamine synthetase FemC |
| SA1142 | glpD | 5.9 | 1.0 | aerobic glycerol-3-phosphate dehydrogenase |
| SA0515 | gltD | 5.6 | 0.9 | glutamate synthase, small subunit |
| SAV0848 | int | 4.3 | 1.2 | excisionase |
| SA0680 | mnhB | 2.2 | 0.5 | Na+/H+ antiporter, MnhB component |
| SA2541 | NA | 7.7 | 0.5 | acetyltransferase, GNAT family |
| SA1050 | NA | 3.6 | 0.5 | hypothetical protein |
| SA0161 | NA | 3.8 | 0.6 | conserved hypothetical protein |
| SA0208 | NA | 3.4 | 1.0 | hypothetical protein |
| SA0480 | NA | 2.0 | 2.7 | hypothetical protein |
| SA0739 | NA | 3.4 | 0.9 | acetyltransferase, GNAT family |
| SA0821 | NA | 2.6 | 0.8 | HD domain protein |
| SA0882 | NA | 2.3 | 0.5 | ABC transporter, ATP-binding protein |
| SA1037 | NA | 2.2 | 3.9 | conserved hypothetical protein |
| SA1335 | NA | 2.1 | 0.7 | conserved hypothetical protein |
| SA1345 | NA | 2.4 | 0.7 | conserved hypothetical protein |
| SA1418 | NA | 2.1 | 0.9 | conserved hypothetical protein |
| SA1499 | NA | 3.2 | 0.4 | conserved hypothetical protein |
| SA1600 | NA | 2.1 | 0.9 | conserved hypothetical protein |
| SA1643 | NA | 2.2 | 0.4 | conserved hypothetical protein |
| SA1658 | NA | 2.4 | 0.7 | hypothetical protein |
| SA1660 | NA | 3.4 | 0.9 | LamB/YcsF family protein |
| SA1930 | NA | 3.8 | 0.6 | conserved hypothetical protein |
| SA1972 | NA | 2.8 | 1.1 | conserved hypothetical protein |
| SA2123 | NA | 2.4 | 0.5 | conserved hypothetical protein |
| SA2272 | NA | 2.4 | 0.4 | conserved hypothetical protein |
| SA2446 | NA | 2.1 | 0.6 | putative epimerase/dehydratase |
| SA2531 | NA | 3.2 | 0.8 | transcriptional regulator, MarR family |
| SA2716 | NA | 2.8 | 0.6 | conserved hypothetical protein |
| SA2731 | NA | 3.9 | 0.6 | cold shock protein, CSD family |

[a]*S. aureus* strain COL locus, unless otherwise indicated (strain preceeds locus identifier).
[b]NA = Not available
[c]description of predicted function FIG. 6G includes a hierarchial clustering, where dendrogram (left) with heat map (right) illustrates the relatedness of transcription profiles of *S. aureus* cells subjected to indicated stresses. Within the heat map, the normalized signal intensity value for each locus represented on the *S. aureus* GeneChip is shown (7775 total). Red indicates high signal intensity; green indicates low intensity in the listed condition. Manganese ($Mn^{2+}$) and Zinc ($Zn^{2+}$)-depleted profiles are 93.8% and 91.2% related to calprotectin treated medium (100% confidence; Pearson correlation average linkage bootstrapping). Transcripts shown in the heatmap as changing expression in any of the three conditions ($Zn^{2+}$ starvation, $Mn^{2+}$ starvation, and calprotectin treatment) are listed in the Supplemental Tables.

Comparison of the global expression changes of *S. aureus* exposed to calprotectin to those observed upon $Mn^{2+}$ starvation, $Zn^{2+}$ starvation, heat shock, cold shock, alkaline shock or acid shock, as well as stringent-response and SOS-response inducing conditions (25)(unpublished Anderson and Dunman) demonstrated that *S. aureus* treated with subinhibitory calprotectin elicit an expression profile most closely resembling that of staphylococci starved for $Zn^{2+}$ and $Mn^{2+}$ (FIG. 6G). Taken together, these data strongly support a model whereby calprotectin prevents *S. aureus* growth through the chelation of nutrient $Mn^{2+}$ and $Zn^{2+}$.

To determine whether calprotectin-mediated cation chelation inhibits bacterial growth in tissue abscesses, the growth of *S. aureus* in abscesses from wildtype mice and calprotectin deficient (S100A9−/−) mice were compared. S100A8 null mice are embryonic lethal (26) and therefore can not be used for these experiments. With reference to FIG. 9A, examination of the livers of wildtype and S100A9 −/− mice 96 hours following intravenous infection revealed that mice lacking calprotectin exhibit increased abscess formation as compared to infected wild-type animals. Additionally, with reference to FIG. 9B, enumeration of bacterial counts from infected livers revealed a significant increase in the number of staphylococci in S100A9-deficient animals as compared to controls.

Figure 10:
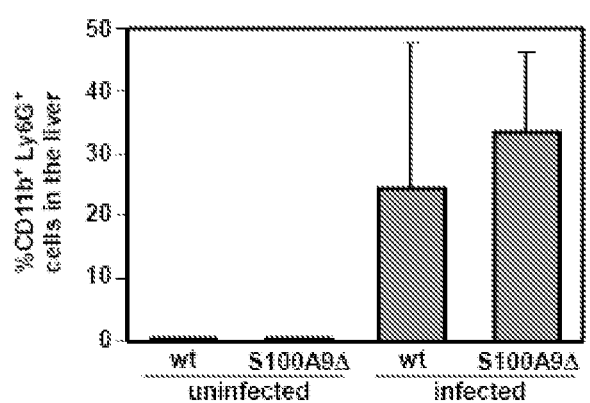
FIG. 10 is a bar graph illustrating the results of a flow cytometry study of liver homogenate from wild-type and calprotectin-deficient mice that were either not infected or infected with S. aureus.

With reference to FIG. 10, wild-type and calprotectin-deficient mice were either not infected or infected with *S. aureus* and the livers harvested 96 hr post-infection. Livers were subsequently homogenized and the percentage of CD11b+/Ly-6G(Gr1)+ cells determined by flow cytometry. Although the immunomodulatory functions of calprotectin (27) may contribute to the sensitivity of calprotectin-deficient animals to *S. aureus* infection, a significant difference in neutrophil recruitment to the livers of these infected animals was not detected by multiparametric FACS-analyses. These data establish calprotectin as a pathophysiologically relevant component of the neutrophil armamentarium to control bacterial infection in vivo.

To assess the effect of calprotectin on nutrient metal availability inside the abscess, Laser Ablation ICP-MS mapping (LA-ICP-MS) was used to image metal distribution in infected animal tissue. LA-ICP-MS allows for two dimensional mapping of trace elements in intact soft tissue (28), and hence was used to generate an image of metal distribution in thin sections from infected murine livers. FIG. 9C includes LA-ICP-MS images of infected organs from wildtype and calprotectin-deficient (S100A9Δ) mice. Theop panel shows infected organs stained with hematoxylin-eosin. The bottom panels shown LA-ICP-MS maps for $Ca^{2+}$ (calcium-44), $Mn^{2+}$ (manganese 55), and $Zn^{2+}$ (zinc 67). Arrows denote the site of abscesses. All data are normalized to levels of carbon-13. Scales are presented in arbitrary units. LA-ICP-MS revealed that staphylococcal liver abscesses from wildtype mice are enriched in $Ca^{2+}$ consistent with the robust immune cell infiltrate to the infection site. In contrast, these abscesses are devoid of detectable $Zn^{2+}$ and $Mn^{2+}$, establishing the abscess as a cation-starved environment. Abscesses from mice lacking calprotectin contain appreciable levels of $Ca^{2+}$, however these levels appear diminished compared to abscesses from wildtype mice, potentially reflecting the $Ca^{2+}$ contribution of calprotectin to the abscess. Furthermore, calprotectin deficient abscesses contain levels of $Mn^{2+}$ equivalent to the surrounding healthy tissue demonstrating the in vivo requirement for calprotectin in $Mn^{2+}$ chelation and removal from the abscess. The absence of calprotectin did not have a significant impact on $Zn^{2+}$ levels in these experiments.

With reference to FIGS. 9D-9F, to confirm these results and validate the use of LA-ICP-MS to image metal distribution in infected animal tissue, abscessed material was extracted from wildtype and calprotectin-deficient animals using Laser Capture Microdissection (LCM) and $Zn^{2+}$, $Mn^{2+}$ and $Ca^{2+}$ concentrations in isolated abscesses were quantitated using ICP-MS. These experiments confirmed that abscesses from mice lacking calprotectin are significantly enriched in $Mn^{2+}$ as compared to those from wildtype mice (FIG. 9E). Taken together, these results establish calprotectin-mediated metal chelation as an immune defense strategy to prevent bacterial outgrowth in tissue abscesses, and demonstrate the utility of LA-ICP-MS to image trace element distribution in healthy and diseased tissue. The inhibition of bacterial nutrient uptake represents a promising alternative area of research for the design of novel antimicrobials and the observed calprotectin-mediated metal chelation provides a specific direction to assess the therapeutic potential of this concept. The results reported here suggest that beyond direct treatment of abscesses with calprotectin protein, non-cytotoxic bioavailable metal ion chelators represent a promising area of investigation for the inhibition of growth of bacterial infections.

Materials and Methods

Imaging Mass Spectrometry.

IMS involves acquiring independent MALDI mass spectra on thin tissue sections mounted on a MALDI target. The intensities of all the mass-to-charge (m/z) signals present in the spectral array are then recorded and plotted in ion density maps or images. By applying IMS to a given tissue section, hundreds of images can be simultaneously recorded in two dimensions at distinct molecular weights. To perform IMS on *staphylococcus*-infected murine tissue, kidneys and livers were sectioned at −20° C. in a cryostat (Leica Microsystems Inc., Bannockburn, Ill., USA) at a thickness of 12 μm. Tissue sections were thaw-mounted onto a gold-coated MALDI target. The target was vacuum desiccated for 30 minutes prior to tissue-fixation by submersion in sequential washes of 70%, 90%, 95% ethanol for 30 seconds each. The plate was returned to the desiccator for 1 hour to allow for complete drying. Matrix (20 mg/ml sinapinic acid in 50:50 acetonitrile/0.2% trifluoroacetic acid in water) was deposited over the entire plate using a glass reagent sprayer to apply uniform crystal coverage. Mass spectral images were acquired on an Autoflex II (Bruker DaltoniK GmbH, Bremen, Germany) MALDI-TOF mass spectrometer equipped with a Smart-Beam laser (Nd:YAG, 355 nm) operated at 200 Hz. Data were obtained in linear mode with an accelerating voltage of 20 kV, an extraction voltage of 18.65 kV, a lens voltage of 6 kV, a delay time of 350 ns, and a detector voltage of 1588 V. Spectra were acquired at a spatial resolution of 100 μm in both x and y by rastering the laser across the tissue. Each spectrum (pixel) was a sum of 100 laser shots. Spectra were compiled into an image file which allowed for visualization of ion intensity as a function of location on the tissue using the Biomap software (Novartis, Basel, Switzerland). Images in FIG. 1 Panel A were taken from BALB/c mice whereas images in FIG. 1 Panel E were taken from C57BL/6 mice. These experiments revealed a similar distribution of calprotectin in both strains of mice.

Isolation and Identification of Abscess Specific Proteins.

Abscessed tissue was dissected from infected organs using a scalpel and transferred to a microcentrifuge tube. Similar areas were also cut out of control tissues for comparison. Proteins were extracted from the tissue using 100 μl of 50% acetonitrile, 0.1% TFA in water with pipette mixing. Extracts were subsequently separated using 1-dimensional SDS-PAGE. A colloidal blue stained protein band present exclusively in the abscessed tissue corresponding to a predicted size of approximately 10,165 Da was then excised from the gel, digested with trypsin, and analyzed using LC-MS/MS. A corresponding molecular weight region of the gel was excised from the uninfected lane and analyzed using LC-MS/MS as a negative control. Exclusion criteria for this analysis included proteins represented by less than three peptides, peptides corresponding to keratin, and peptides corresponding to proteins from species other than *Mus musculus* or *Staphylococcus aureus*.

Laser Capture Microdissection (LCM).

Murine kidneys were sectioned into 5 μM sections and transferred to glass slides. The tissue slides were fixed as follows: 70% ethanol for 30 seconds, 95% ethanol for 1 minute, 100% ethanol for 1 minute, 100% ethanol for 1 minute, xylene for 2 minutes, xylene for 3 minutes. The slides were removed from the xylene solution and allowed to air-dry for 5 minutes. The fixed slides were loaded into a Veritas system Laser Capture Microdissection (LCM) machine (Molecular Devices). The tissue samples were microdissected at 10× magnification, and with a power range of 70 mW-100 mW and pulse range 2,500 μs-11,000 μs. The polymer sides of the LCM caps containing the captured sections were subjected to ICP-MS as described below.

Inductively Coupled Plasma-Mass Spectrometry (ICP-MS). For measuring the effect of calprotectin on cation concentrations, calprotectin (75.92 μM) or a buffer control was incubated with 0.8 ml of NRPMI containing 100 μM $CaCl_2$, 25 μM $ZnCl_2$, 1 mM $MgCl_2$, 25 μM $MnCl_2$, and 5 μM $FeSO_2$ overnight at 4° C. Samples were subsequently passed through a centricon column with a 5,000 Da cutoff by spinning at 4000 RPM for 30 minutes. The flow-through was collected, mixed with high purity 15N nitric acid (SEASTAR™), and heated in sealed SAVILLEX® PFA Teflon vials at 130° C. for three hours. Samples were subsequently analyzed as described below.

Figure 9:
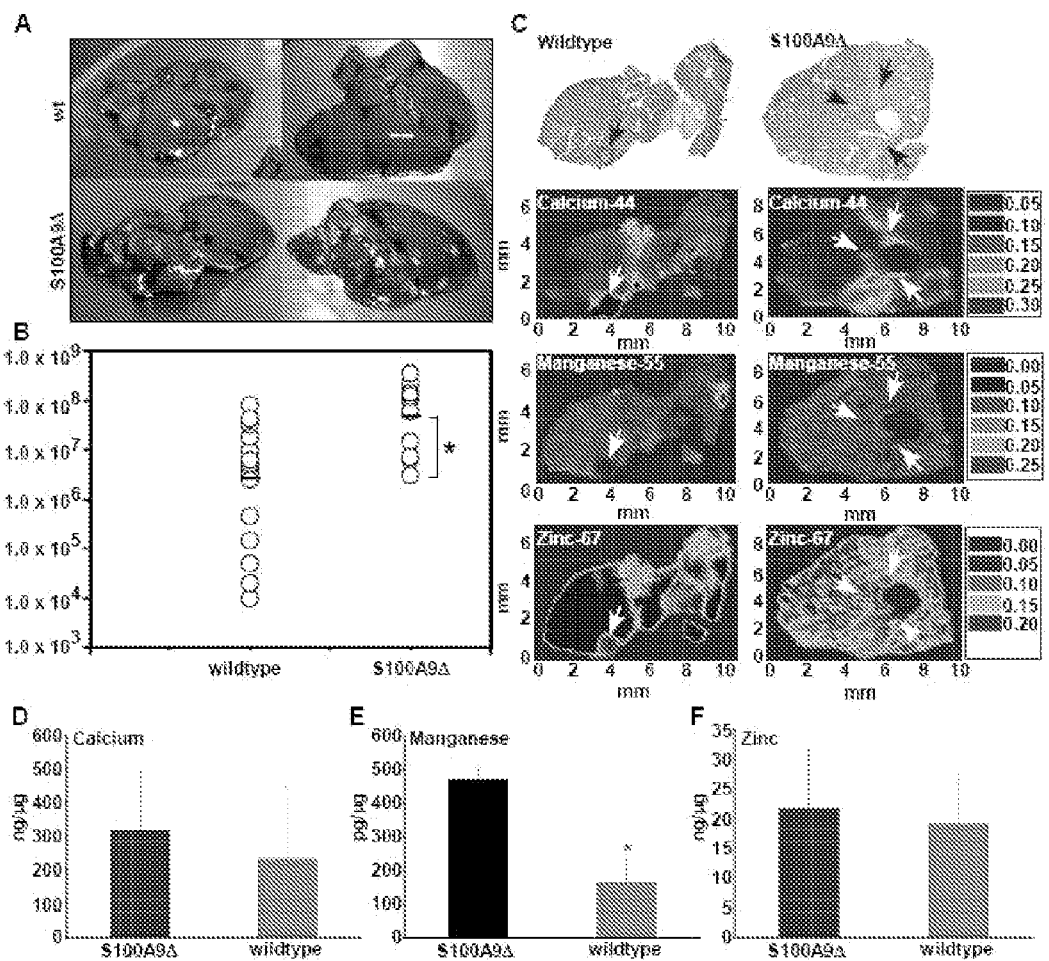
FIG. 9A includes a series of photographs of livers dissected from C57BL/6 wild-type and S100A9Δ mice infected with S. aureus 96 hr post-infection.
FIG. 9B is a graph illustrating S. aureus multiplication in infected livers as measured by tissue homogenization, dilution, and colony formation on agar media 96 hr post-infection, where each circle represents a positive culture from a single liver.
FIG. 9C includes a series of LA-ICP-MS images of infected organs from wildtype and calprotectin-deficient (S100A9Δ) mice, where the top panel shows infected organs stained with hematoxylin-eosin, and the bottom panels shows LA-ICP-MS maps for $Ca^{2+}$ (calcium-44), $Mn^{2+}$ (manganese 55), and $Zn^{2+}$ (zinc 67).
FIGS. 9D-9F are a series of bar graphs showing quantitative determinations of metal concentrations (calcium, manganese, and zinc, respectively) in abscessed tissue from wildtype or calprotectin-deficient (S100A9Δ) mice extracted using laser capture microdissection (LCM).

For determining the concentrations of the metal in abscessed tissue, abscesses were extracted using LCM as described above. Each LCM cap contained approximately equal amounts of abscessed material. Samples were then solublized for approximately 8 hours in concentrated nitric acid (trace metal free) at 130° C. The concentration of $Zn^{2+}$, $Mn^{2+}$ and $Ca^{2+}$ were subsequently analyzed as described below, and normalized to the dry weight of the sample. The values listed in FIG. 9 represent the concentration of metal present in the abscessed tissue and any residual metal contaminating the LCM caps.

Sample analysis was performed by Applied Speciation (Tukwila, Wash.). A total of 10 mL of 5% $HNO_3$ (v/v) was added to each digestion vessel followed by oven digestion overnight at 80° C. The digests were allowed to cool to room temperature and were analyzed by inductively coupled plasma dynamic reaction cell mass spectrometry (ICP-DRC-MS, Perkin Elmer DRC II). Aliquots of each sample are introduced into a radio frequency (RF) plasma where energy-transfer processes cause desolvation, atomization, and ionization. The ions are extracted from the plasma through a differentially-pumped vacuum interface and travel through a pressurized chamber (DRC) containing a specific reactive gas (see tables) which preferentially reacts with interfering ions of the same target mass to charge ratios (m/z). A solid-state detector detects ions transmitted through the mass analyzer, on the basis of their mass-to-charge ratio (m/z), and the resulting current is processed by a data handling system. Different reaction gases and settings are applied depending on the target analyte and projected interference. Comparison of the different isotopes, reaction gases, and reaction gas settings allow for interference monitoring and selection of optimum instrument settings depending on each sample matrix type and element.

TABLE 7

ICP-DRC-MS Operating Conditions and Parameters

| Parameter | Setting/Type |
|---|---|
| Nebulizer | Meinhard Type A Quartz |
| RF Power | 1200 W |
| Plasma Ar Flow | 15 L/min |
| Nebulizer Ar Flow | 0.87 L/min |
| Injector | 2.0 mm I.D. Quartz |
| Monitored ion (m/z) | $^{64}Zn^+$, $^{66}Zn^+$, $^{40}Ca^+$, $^{43}Ca^+$, $^{44}Ca^+$, $^{54}Fe^+$, $^{56}Fe^+$, |
| Reaction Gas | $NH_3$ |
| $NH_3$ Flow | 0.8 mL/min |
| RPq | 0.7 |

TABLE 8

ICP-DRC-MS Operating Conditions and Parameters (for $^{55}Mn^+$ detection)

| Parameter | Setting/Type |
|---|---|
| Nebulizer | Meinhard Type A Quartz |
| RF Power | 1200 W |
| Plasma Ar Flow | 15 L/min |
| Nebulizer Ar Flow | 0.87 L/min |
| Injector | 2.0 mm I.D. Quartz |
| Monitored ion (m/z) | $^{55}mn^+$ |
| Reaction Gas | none |
| RPq | 0.25 |

Laser Ablation Inductively Coupled Plasma Mass Spectrometry (LA-ICP-MS).

LA-ICP-MS was performed on 30 µM sections from murine liver tissue prepared as described below. A Nd:YAG laser system which operates at 266 nm (quadrupled wavelength) (Laser 200+, Cetac, USA) was used throughout the study with a large ablation cell from CETAC. Argon gas was used during ablation. The samples were ablated in scan mode using a 100 µm spot size with a scan speed of 25 µm/s, 20 Hz frequency and 100% energy (~3.6 mJ). The ICP-MS system was a 7500c from Agilent (USA) used without reaction gas. The laser was directly coupled into the ICP-MS, by re-routing the nebulizer gas (argon) through the ablation cell using polyethylene tubing to connect the laser exit directly to the torch. Parameters were optimised either under wet plasma conditions before connecting the laser, or in the case of the nebulizer gas, with the laser connected to the system. The images were generated using Sigmaplot version 10.0.

TABLE 9

ICP-MS Operating Conditions and Parameters

| Parameter | Setting/Type |
|---|---|
| Nebulizer | none |
| RF Power | 1580 W |
| Plasma Ar Flow | 15 L/min |
| Nebulizer Ar Flow | 1.5 L/min |
| Injector | 2.0 mm I.D. Quartz |
| Monitored ion (m/z) | $^{55}Mn^+$, $^{64}Zn^+$, $^{67}Zn^+$, $^{44}Ca^+$, $^{63}Cu^+$, $^{57}Fe^+$, $^{31}P^+$, $^{32}S^+$, $^{24}Mg^+$, $^{3}C^+$ |
| Reaction Gas | none |

Bacterial Strains, Media and Growth Conditions.

*S. aureus* Newman, a human clinical isolate (1), was used for all experiments in this study with the exception of the PMN lysate antimicrobial assays which employed *S. aureus* RN6390. This decision was made based on our observations that RN6390 exhibits increased sensitivity to neutrophil-dependent killing mechanisms (data not shown). mntR was inactivated by following a protocol described by Bae and Schneewind (2). Briefly, sequences flanking mntR were PCR amplified with primers SAV0634-5'1-AttB 1 (GGGGA-CAAGTTTGTACAAAAAAGCAGGCT-ACTGTACCA-CAAACTATCCC) (SEQ ID NO: 5) and SAV0634-3'1-Sal1 (CCCCGTCGACCCATTATTCGTAAGGATTGCC) (SEQ ID NO: 6) for the upstream fragment and primers SAV0634-3'2-AttB2 (GGGGACCACTTTGTACAAGAAAGCTGGG-TAGGTAAGTCTAAAGTCTAACG) (SEQ ID NO: 7) and SAV0634-5'2-Sal1 (CCCCGTCGACGTCAGTTAC-GAAAATGCAATG) (SEQ ID NO: 8) for the downstream fragment. The PCR fragments were then assembled into pCR2.1 (Invitrogen) and recombined into pKOR1(2). Inactivation of mntR was achieved by allelic replacement with pKOR1ΔmntR and mutations subsequently verified by PCR. Strains defective in mntA or mntB were obtained from the Phoenix Library of defined *S. aureus* transposon mutations (3). *S. aureus* growth was monitored in TSB or NRPMI (Chelex-treated RPMI) supplemented with 100 µM $CaCl_2$, 25 µM $ZnCl_2$, 1 mM $MgCl_2$, 25 µM $MnCl_2$, and 5 µM $FeSO_4$. The sensitivity of *S. aureus* to calprotectin was assessed by conducting a dose response curve. Cultures were grown at 37° C. with shaking at 180 RPM in a 96-well microtiter plate and bacterial growth was monitored by measuring the increase in O.D.$_{600}$ over time. For microarray analyses overnight cultures of Newman were used to inoculate (1:100 dilution; flask to volume ratio of 5:1) 50 ml RPMI broth. RPMI was first incubated in the presence of calprotectin and then filtered to remove the protein and any metals it may have chelated. Cultures were incubated at 37° C. with shaking at 225 RPM until reaching O.D.$_{600}$=0.25. Twenty ml of cells was added to an equal volume of ice cold acetone::ethanol (1:1) and stored at −80° C. for RNA isolation, as described below.

Co-Sedimentation Assay.

*S. aureus* (500 µl of a culture at O.D.$_{600}$ 0.5) was mixed with purified calprotectin (0-250 µg/ml) at room temperature for 45 minutes with shaking at 180 RPM. Following incubation, cells were pelleted and the supernatant harvested. The cells were subsequently washed 3× in tryptic soy broth (TSB) medium and cells and supernatant fractions were mixed with sodium dodecyl sulfate (SDS)-loading buffer. To test for an interaction between S100A8 and whole cell *S. aureus*, the whole cell lysates and harvested supernatant fractions were run on a 10% SDS-polyacrylamide gel. Separated proteins were subjected to immunoblot using antisera specific to S100A8 (Santa Cruz Biotechnology).

Dialysis Growth Assay.

Dialysis tubing (Spectra/Por Biotech) with a cutoff of 5,000 Da was cut into 10 mm sections and one end tied off in a knot. The tubing was prepared by first boiling for 1 hour in 1 mM EDTA, followed by boiling for 2 hours in distilled $H_2O$ to remove any bound metals. One ml of either buffer or calprotectin (2.5 mg/ml stock) was added to tubing which was tied at the open end, and placed into a 50 ml centrifuge tube containing 5 ml of TSB. The media were then inoculated with *S. aureus* and grown overnight at 37° C. with shaking at 180 RPM. The following morning bacterial growth was tracked by measuring changes in $O.D._{600}$.

Metal-Reversible Antimicrobial Assays.

To assess the metal binding properties of calprotectin we added an inhibitory dose of calprotectin (75 µg/ml) to *S. aureus* cells growing in chemically defined NRPMI medium. $Mn^{2+}$ and $Zn^{2+}$ were subsequently added to the growing staphylococcal culture in excess (1 mM) and growth monitored by measuring the increase in $O.D._{600}$ over time.

$Mn^{2+}$ Toxicity Assays.

Wild-type and a ΔmntR mutant strain were grown in high levels of $Mn^{2+}$ (1 mM) with or without calprotectin (40 µg/ml). Cell growth was monitored by measuring the increase in $O.D._{600}$ over time.

PMN Lysate Antimicrobial Assays.

PMNS were extracted from peripheral blood of human volunteers provided by the Cooperative Human Tissue Network at Vanderbilt University or from cellular filtrates from healthy human blood provided by the American Red Cross. PMNs were isolated from peripheral blood by differential migration in Ficoll-Paque PLUS and hypotonic lysis. Cells were re-suspended in lysis buffer (20 mM Tris pH 8.0, 120 mM NaCl, 3 mM $CaCl_2$) and sonicated. The sonicated samples were subsequently centrifuged at 13,000×g for 10 minutes at 4° C. The supernatant was then transferred to an ultracentrifuge tube and centrifuged at 80,000 rpm (289,000×g) for 10 minutes at 4° C. The supernatant was subsequently filtered through a 0.2 µM filter, mixed with either an equal volume of RPMI or RPMI containing excess $Mn^{2+}$ (1 mM), and used for growth inhibition assays. Alternatively, cell lysates were mixed with protein G complexed with either 100 µg of monoclonal antibody to calprotectin (Calgranulin A/B (5.5)), or an isotype-matched control antibody (ebioscience) for two hours at 4° C. The preparation was then centrifuged for 1 minute at 1,000×g, the supernatant harvested, filtered through a 0.2 micron filter, and tested for anti-staphylococcal activity.

Phagocytosis Assay.

Mice were injected intraperitoneally with 1 ml of 3% thioglycollate. After 16 hours mice were sacrificed, and 10 ml of PBS injected into the peritoneal cavity. The injected wash was subsequently withdrawn while gently massaging the peritoneal wall. Peritoneal Exudate Cells (PECs) were subsequently resuspended in FACS buffer (phosphate buffered saline, pH 7.5, 0.05% $NaN_3$, 5% fetal bovine serum) for flow cytometry analyses or RPMI/H for phagocytic killing assays. Flow cytometry analyses revealed that greater than 75% of the total PECs were neutrophils (CD11b+/Ly6G+).

PECs were counted using a hemacytometer following trypan blue staining and adjusted to a density of $1\times10^7$ cells/ml in RPMI/H. Killing during a 2 hour incubation at 37° C. was assessed by combining 100 µl PECs with 100 µl of *S. aureus* ($2\times10^7$ cells/ml) that were opsonized with 50% normal mouse serum. Cells were subsequently treated with saponin (0.1% final) and incubated on ice for 15 minutes. Bacterial enumeration was performed following serial dilutions and plating on TSB media.

Protein Expression and Purification.

Recombinant human S100A8 and S100A9 protein were expressed and purified as described previously (4, 5). Briefly, competent *Escherichia coli* strain BL21 (DE3) cells (Novagen, Madison, Wis., USA) were transformed with the pET1120-MRP8 wt and pET1120-MRP14 wt vectors. Transformed cells were grown at 37° C. in (LB) media supplemented with 100 g/ml ampicillin. Protein was expressed into inclusion bodies and harvested by centrifugation at 7000×g at 4° C. Cells were lysed by sonication. Inclusion bodies were washed, solubilized in a refolding buffer, and purified over hydroxyapatite (Bio-Rad, Hercules, Calif., USA) and ResourceQ (GE Healthcare Bio-Sciences, Uppsala, Sweden) anion exchange resin.

Fluorescence Spectroscopy.

Prior to experiments, S100A8/S100A9 was treated with 5 mM BAPTA and 10 mM DTT for 24 h at 25° C. to remove all divalent cations and reduce all cysteines. BAPTA and DTT were removed using a 50 mL desalting column (GE Healthcare) that had been extensively equilibrated in chelex treated 20 mM Tris at pH 7.5. All fluorescence cells were washed with a BAPTA solution followed by extensive washing with chelex treated buffer. Steady-state fluorescence experiments were performed on a SPEX FLUOROMAX spectrofluorimeter. Emission spectra were collected in 1 nm increments between 300 and 400 nm with the excitation wavelength for tryptophan set at 280 nm. S100A8/S100A9 concentration was 5 µM and data were collected at ambient temperature in a 3 mL cuvette.

Mouse Model of Infection.

Six to eight week old C57BL/6 (The Jackson Laboratory) or S100A9 −/− mice were infected with $1\times10^6$ or $1\times10^5$ colony forming units of *S. aureus* suspended in phosphate buffered saline (PBS) by injection into the retro-orbital vein complex. Four days (96-hours) post-infection, mice were euthanized with $CO_2$ and the kidneys and liver removed and analyzed for abscess formation. Organs were subsequently prepared for FACS-based analyses as described or prepared for IMS, ICP-MS or IHC following flash freezing or fixing in 10% formalin. To partially or fully deplete PMNs, we administered a rat IgG2b anti-Gr-1 mAb RB6-8C5 as described by others (6, 7). S100A9 −/− mice represent $6^{th}$ generation backcrossed with C57BL/6. All mice were maintained in compliance with Vanderbilt's institutional animal care and use committee regulations.

Histological Tissue Analysis.

Parafin-embedded mouse tissues were stained with hematoxylin and eosin. Frozen tissue sections were stained with antiserum specific to S100A8 (Santa Cruz Biotechnology) by the Vanderbilt University Medical Center Immunohistochemistry Core Laboratory.

Flow Cytometry. Antibodies and reagents for cell surface staining were purchased from BD Pharmingen. Total erythrocyte-free kidney and liver lymphocytes and leukocytes of individual, age matched (~7 weeks old) C57BL/6 female mice infected with *S. aureus* ($1\times10^6$ CFU) or uninfected as described above, were analyzed by four-color flow cytometric analysis. Neutrophils were gated as $Ly6G^+$, $CD11b^+$, $B220^-$, $F480^-$ as described previously. Four-color flow cytometry was performed with a FACSCALIBUR® instrument (Becton Dickinson) and the data were analyzed using FlowJo software (Treestar Inc).

RNA purification. For RNA isolation, aliquots of acetone: ethanol cell suspensions were pelleted by centrifugation at 3000 RPM at 4° C. for 10 min in a tabletop centrifuge. The supernatant was discarded and cell pellet was resuspended in 500 ul TE buffer (10 mM Tris, 1 mM EDTA pH 8.0). Cell suspensions were then transferred to BIO101 lysing matrix B tubes and were mechanically disrupted in a FastPrep 120 shaker. Cell debris was collected by centrifugation in a microcentrifuge at 4° C. for 15 min. Supernatants were used for RNA isolation using the Qiagen RNEASY® Tissue Kit following manufacturer's recommendations. RNA concentration was determined spectrophotometrically (OD 1.0=40 μg ml$^{-1}$). The RNA integrity of ribosomal RNA was evaluated on 1.2% agarose-0.66M formaldehyde denaturing gels.

Nucleic acid labeling and GENECHIP® analysis. Ten micrograms of total bacterial RNA from each sample was labeled and hybridized to *S. aureus* GENECHIP® following the manufacturer's recommendations for antisense prokaryotic arrays (Affymetrix; Santa Clara, Calif.). Briefly, RNA was reverse transcribed in the presence of exogenous poly-A control RNAs (Affymetrix). Purified cDNA was then fragmented with DNase I (Amersham BioSciences; Piscataway, N.J.) and 3' end-labeled with biotin using the Enzo Bioarray Terminal Labeling Kit (Enzo Life Sciences; Farmingdale, N.Y.). DNA was fragmented with DNase I and 3' end-labeled as above. GENECHIP® were washed, stained, and scanned as previously described (8, 9). Commercially available GeneChips were used in this study representing >3,300 *S. aureus* open reading frames and >4,800 intergenic regions from strains N315, Mu50, NCTC 8325, and COL. GENECHIP® signal intensity values for each qualifier at each replicate time point (n≥2) were averaged and normalized to control oligo signals using GeneSpring 7.2 software (Silicon Genetics; Redwood City, Calif.).

Statistical Analysis.

Two-tailed t-tests were used to determine significant differences (P≤0.05); Error bars represent the standard deviation of at least three replicates, and all experiments were performed in triplicate. Pearson correlation average linkage bootstrapping was used to compare *S. aureus* transcriptional profiles.

Throughout this document, various references are mentioned. All such references are incorporated herein by reference, including the references set forth in the following list:

REFERENCES

1. F. D. Lowy, *N Engl J Med* 339, 520 (Aug. 20, 1998).
2. M. Stoeckli, P. Chaurand, D. E. Hallahan, R. M. Caprioli, *Nat Med* 7, 493 (April, 2001).
3. M. L. Reyzer, Y. Hsieh, K. Ng, W. A. Korfmacher, R. M. Caprioli, *J Mass Spectrom* 38, 1081 (October, 2003).
4. M. L. Reyzer, R. M. Caprioli, *Curr Opin Chem Biol* 11, 29 (February, 2007).
5. J. M. Voyich et al., *J Immunol* 175, 3907 (Sep. 15, 2005).
6. I. Dale, P. Brandtzaeg, M. K. Fagerhol, H. Scott, *Am J Clin Pathol* 84, 24 (July, 1985).
7. K. Odink et al., *Nature* 330, 80 (Nov. 5-11, 1987).
8. M. M. Wilkinson et al., *J Cell Sci* 91 (Pt 2), 221 (October, 1988).
9. M. Steinbakk et al., *Lancet* 336, 763 (Sep. 29, 1990).
10. H. J. Loomans, B. L. Hahn, Q. Q. Li, S. H. Phadnis, P. G. Sohnle, *J Infect Dis* 177, 812 (March, 1998).
11. D. Lusitani, S. E. Malawista, R. R. Montgomery, *Infect Immun* 71, 4711 (August, 2003).
12. P. G. Sohnle, M. J. Hunter, B. Hahn, W. J. Chazin, *J Infect Dis* 182, 1272 (October, 2000).
13. J. E. Posey, F. C. Gherardini, *Science* 288, 1651 (Jun. 2, 2000).
14. B. Sugarman, *Rev Infect Dis* 5, 137 (January-February, 1983).
15. A. R. Murthy, R. I. Lehrer, S. S. Harwig, K. T. Miyasaki, *J Immunol* 151, 6291 (Dec. 1, 1993).
16. M. J. Hunter, W. J. Chazin, *J Biol Chem* 273, 12427 (May 15, 1998).
17. P. A. Clohessy, B. E. Golden, *Scand J Immunol* 42, 551 (November, 1995).
18. B. Johne et al., *Mol Pathol* 50, 113 (June, 1997).
19. A. Voganatsi, A. Panyutich, K. T. Miyasaki, R. K. Murthy, *J Leukoc Biol* 70, 130 (July, 2001).
20. I. P. Korndorfer, F. Brueckner, A. Skerra, *J Mol Biol* 370, 887 (Jul. 27, 2007).
21. J. Delabie, C. de Wolf-Peeters, J. J. van den Oord, V. J. Desmet, *Clin Exp Immunol* 81, 123 (July, 1990).
22. M. J. Robinson, P. Tessier, R. Poulsom, N. Hogg, *J Biol Chem* 277, 3658 (Feb. 1, 2002).
23. M. J. Horsburgh et al., *Mol Microbiol* 44, 1269 (June, 2002).
24. K. Hantke, *Curr Opin Microbiol* 4, 172 (2001).
25. K. L. Anderson et al., *J Bacteriol* 188, 6739 (October, 2006).
26. R. J. Passey et al., *J Immunol* 163, 2209 (Aug. 15, 1999).
27. T. Vogl et al., *Nat Med* 13, 1042 (September, 2007).
28. A. Kindness, C. N. Sekaran, J. Feldmann, *Clin Chem* 49, 1916 (November, 2003).
29. B. D. Corbin, E. H. Seeley, A. Raab, J. Feldmann, M. R. Miller, V. J. Torres, K. L. Anderson, B. M. Dattilo, P. M. Dunman, R. Gerads, R. M. Caprioli, W. Nacken, W. J. Chazin, E. P. Skaar, *Science* 319 (5865), 962-5 (Feb. 15, 2008).

MATERIALS AND METHODS REFERENCES

1. E. S. Duthie, L. L. Lorenz, *J Gen Microbiol* 6, 95 (February, 1952).
2. T. Bae, O. Schneewind, *Plasmid* (Jul. 25, 2005).
3. T. Bae et al., *Proc Natl Acad Sci USA* 101, 12312 (Aug. 17, 2004).
4. M. J. Hunter, W. J. Chazin, *J Biol Chem* 273, 12427 (May 15, 1998).
5. S. Yui, Y. Nakatani, M. J. Hunter, W. J. Chazin, M. Yamazaki, *Mediators Inflamm* 11, 165 (June, 2002).
6. M. Verdrengh, A. Tarkowski, *Infect Immun* 65, 2517 (July, 1997).
7. A. P. Vassiloyanakopoulos, S. Okamoto, J. Fierer, *Proc Natl Acad Sci USA* 95, 7676 (Jun. 23, 1998).
8. K. E. Beenken et al., *J Bacteriol* 186, 4665 (July, 2004).
9. P. M. Dunman et al., *J Bacteriol* 183, 7341 (December, 2001).

What is claimed is:

1. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, and wherein the manganese ion chelator is administered at or near a site of infection or a site associated with a risk of infection.

2. The method of claim 1, wherein the manganese ion chelator is also a zinc ion ($Zn^{2+}$) chelator.

3. The method of claim 1, wherein the manganese ion chelator is a protein.

4. The method of claim 3, wherein the protein is an isolated calprotectin heterodimer.

5. The method of claim 3, wherein the protein is a fragment of a calprotectin heterodimer including a $Mn^{2+}$ binding motif and a $Zn^{2+}$ binding motif.

6. The method of claim 4, wherein the calprotectin heterodimer includes:
    an S100A8 polypeptide, or a fragment of the S100A8 polypeptide that includes a $Mn^{2+}$ binding motif and a $Zn^{2+}$ binding motif, and
    an S100A9 polypeptide, or a fragment of the S100A9 polypeptide that includes a $Mn^{2+}$ binding motif and a $Zn^{2+}$ binding motif.

7. The method of claim 6, wherein the S100A8 includes the amino acid sequence of SEQ ID NO: 1.

8. The method of claim 7, wherein the S100A9 includes the amino acid sequence of SEQ ID NO: 2.

9. The method of claim 6, wherein the S100A8 includes the amino acid sequence of SEQ ID NO: 3.

10. The method of claim 9, wherein the S100A9 includes the amino acid sequence of SEQ ID NO: 4.

11. The method of claim 6, wherein the S100A9 includes the amino acid sequence of SEQ ID NO: 2.

12. The method of claim 6, wherein the S100A9 includes the amino acid sequence of SEQ ID NO: 4.

13. The method of claim 1, wherein the microbe is a bacterial pathogen.

14. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the bacterial pathogen is a *Staphylococcus*.

15. The method of claim 14, wherein the bacterial pathogen is *Staphylococcus aureus*.

16. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the microbe is an antibiotic-resistant strain of a bacterial pathogen.

17. The method of claim 16, wherein the bacterial pathogen is a *Staphylococcus*.

18. The method of claim 17, wherein the bacterial pathogen is *Staphylococcus aureus*.

19. The method of claim 1, wherein the microbe is a fungal pathogen.

20. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered before the microbial infection or the abscessed tissue occurs in the subject.

21. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered after the microbial infection or the abscessed tissue occurs in the subject.

22. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered to the abscessed tissue.

23. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered at or near a site of infection.

24. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered at or near a site associated with a risk of infection.

25. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered topically.

26. A method for treating a microbial infection or an abscessed tissue in a subject, comprising: administering to the subject an effective amount of a manganese ion ($Mn^{2+}$) chelator, wherein the manganese ion chelator is bound with $Ca^{2+}$ before administration, wherein the manganese ion chelator is administered by injection.

* * * * *